United States Patent
Bernini et al.

(10) Patent No.: US 12,201,690 B2
(45) Date of Patent: Jan. 21, 2025

(54) FORMULATIONS/COMPOSITIONS COMPRISING IBRUTINIB

(71) Applicant: Janssen Pharmaceutica NV, Beerse (BE)

(72) Inventors: Maristella Bernini, Beerse (BE); Wenyu Dong, The Hague (NL); Rene Holm, Woluwe Saint Pierre (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 16/441,497

(22) Filed: Jun. 14, 2019

(65) Prior Publication Data
US 2019/0381174 A1    Dec. 19, 2019

(30) Foreign Application Priority Data

Jun. 15, 2018    (EP) .................................. 18177987

(51) Int. Cl.
| | |
|---|---|
| A61K 47/10 | (2017.01) |
| A61K 31/519 | (2006.01) |
| A61K 47/02 | (2006.01) |
| A61K 47/12 | (2006.01) |
| A61K 47/26 | (2006.01) |
| A61K 47/38 | (2006.01) |
| A61P 35/00 | (2006.01) |
| A61P 35/02 | (2006.01) |

(52) U.S. Cl.
CPC ............ *A61K 47/10* (2013.01); *A61K 31/519* (2013.01); *A61K 47/02* (2013.01); *A61K 47/12* (2013.01); *A61K 47/26* (2013.01); *A61K 47/38* (2013.01); *A61P 35/00* (2018.01); *A61P 35/02* (2018.01)

(58) Field of Classification Search
CPC ...... A61K 31/519; A61K 47/02; A61K 47/10; A61K 47/12; A61K 47/26; A61K 47/38; A61K 9/0095; A61K 9/10; A61P 35/00; A61P 35/02
USPC ...................................................... 514/262.1
See application file for complete search history.

(56) References Cited

U.S. PATENT DOCUMENTS

| | | | |
|---|---|---|---|
| 2009/0221563 A1* | 9/2009 | Biesmans et al. | A61K 31/5415 514/226.5 |
| 2015/0118222 A1 | 4/2015 | Levy et al. | |
| 2016/0287594 A1* | 10/2016 | Gupta | A61P 43/00 |

FOREIGN PATENT DOCUMENTS

| | | |
|---|---|---|
| JP | 2016-534157 A | 11/2016 |
| WO | 2008/039218 A2 | 4/2008 |
| WO | 2008/121742 A2 | 10/2008 |
| WO | 2011/153514 A2 | 12/2011 |
| WO | 2013/184572 A1 | 12/2013 |
| WO | 2014/004707 | 1/2014 |
| WO | 2015/084892 A1 | 6/2015 |
| WO | 2015/187848 A1 | 12/2015 |
| WO | 2016/019341 A1 | 2/2016 |
| WO | 2016022942 A1 | 2/2016 |
| WO | 2016141068 A1 | 9/2016 |
| WO | 2016/156127 A1 | 10/2016 |
| WO | 2016/160604 A1 | 10/2016 |
| WO | 2016/164404 | 10/2016 |
| WO | 2017/125423 | 7/2017 |
| WO | 2017/125424 A1 | 7/2017 |
| WO | 2017/205843 A1 | 11/2017 |

OTHER PUBLICATIONS

European Medicines Agency (hereinafter EMA) (Oct. 9, 2017 EMA/CHMP/272866/2013 Committee for Human Medicinal Products (CHMP), pp. 1-15) .*
Marathon Pharmaceuticals, LLC, Emflaza (deflazacort) Prescribing Information, Revised Feb. 2017, FDA, pp. 1-26. (Year: 2017).*

* cited by examiner

*Primary Examiner* — Jeffrey S Lundgren
*Assistant Examiner* — Heather Dahlin
(74) *Attorney, Agent, or Firm* — BakerHostetler

(57) ABSTRACT

Disclosed are formulations/compositions comprising ibrutinib:

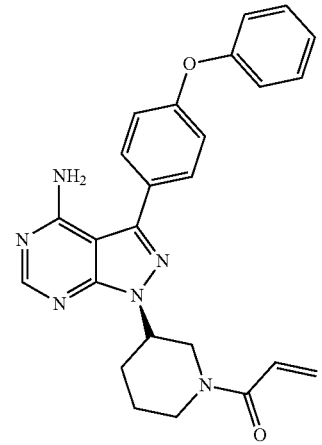

as well as processes for preparing such formulations/compositions and methods of treatment of a disease or condition that comprises the use of such formulations/compositions.

12 Claims, No Drawings

FORMULATIONS/COMPOSITIONS COMPRISING IBRUTINIB

CROSS REFERENCE TO RELATED APPLICATIONS

This application is a U.S. Non-Provisional application, which claims priority from European Application 18177987.7 filed on 15 Jun. 2018. The complete disclosures of the aforementioned related patent applications are hereby incorporated herein by reference for all purposes.

FIELD OF THE INVENTION

The present invention relates to formulations of a Bruton's tyrosine kinase (BTK) inhibitor, particularly ibrutinib. It also relates to processes for preparing such formulations/compositions comprising ibrutinib as well as methods of using such formulations/compositions in the treatment of hematological malignancies.

BACKGROUND OF THE INVENTION

Ibrutinib is an organic small molecule having IUPAC name 1-[(3R)-3-[4-amino-3-(4-phenoxyphenyl)pyrazolo[3,4-d]pyrimidin-1-yl]piperidin-1-yl]prop-2-en-1-one. It is described in a number of published documents, including international patent application WO 2008/039218 (Example 1b), and is described as an irreversible inhibitor of Btk.

Ibrutinib plays a role in targeting B-cell malignancies. Ibrutinib blocks signals that stimulate malignant B cells to grow and divide uncontrollably. It is therefore being studied in clinical trials for various hematological malignancies such as chronic lymphocytic leukemia, mantle cell lymphoma, diffuse large B-cell lymphoma, Waldenstrom's macroglobulinemia and multiple myeloma. It has also received regulatory approval in some counties for certain conditions. For example, it was approved by the US FDA in November 2013 for the treatment of mantle cell lymphoma, in February 2014 for the treatment of chronic lymphocytic leukemia and in January 2015 for the treatment of Waldenstrom's macroglobulinemia. It is marketed under the trade name Imbruvica®.

Crystalline forms of ibrutinib are disclosed in WO 2013/184572. Formulations of ibrutinib have been described in the literature, for example in WO 2014/004707, US 2014/0336203, WO 2016/022942, WO 2016/141068, WO 2016/164404, WO 2017/125423 and WO 2017/125424. Co-crystals of ibrutinib are also disclosed, for example in WO 2016/160604 and WO 2016/156127.

Alternative formulations of ibrutinib are required and/or desired, in particular for the pediatric population. In the case of pediatric formulations, there are a number of possible alternatives that may be pursued. In the case of suspensions, there are a number of challenges including shelf-life stability.

SUMMARY OF THE INVENTION

In one aspect, there is now provided a pharmaceutical formulation (intended to form a suspension) comprising:
(i) ibrutinib, wherein ibrutinib is a compound with the structure of Compound 1,

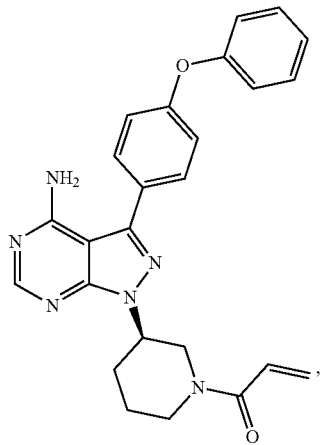

Compound 1 and a suspending agent, optionally in the presence of a pharmaceutically acceptable carrier; and
(ii) at least one preservative that is benzyl alcohol;
and, optionally, one or more other pharmaceutically acceptable excipients,
which formulation may be referred to herein as a "formulation of the invention".

The formulation of the invention may be reconstitutable, i.e. it may not contain a pharmaceutically acceptable carrier (e.g., purified water or another suitable carrier as defined herein), or it may be a suspension product already containing the carrier (e.g., purified water or another suitable carrier as defined herein). Hence, in the latter case, there is provided a pharmaceutical formulation in the form of a suspension comprising: (i) ibrutinib, wherein ibrutinib is a compound with the structure of Compound 1,

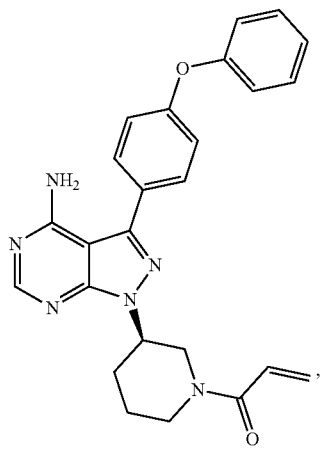

Compound 1 suspended in a pharmaceutically acceptable carrier; and
(ii) at least one preservative that is benzyl alcohol;
and, optionally, one or more other pharmaceutically acceptable excipients.

The invention thus concerns a variety of formulations that are suspensions containing ibrutinib, or a pharmaceutically acceptable salt or solvate thereof, and wherein benzyl alcohol is the main preservative present, and the formulations may further contain one or more further pharmaceutically acceptable excipients. The invention further concerns methods for preparing such pharmaceutical formulations. The invention yet further concerns the use of such formulations as a pharmaceutical, for instance in the treatment of a disease as described hereinafter. The invention also concerns a method of treating a disease in a patient in need of such treatment, comprising administering to the patient a therapeutically effective amount of such a pharmaceutical formulation.

It is indicated herein that benzyl alcohol is the main preservative present in the formulations of the invention, which is also understood by the skilled person to encompass suitable equivalents of benzyl alcohol that achieve the same effect, that is have the same, or similar, efficacy in terms of preservation, has the same, or similar, stability profile and/or does not form co-crystals with the active ingredient (ibrutinib). All of the foregoing may be tested in the tests used in the experimental as described hereinafter. For instance: sufficient preservation may be tested as described in the PETs (preservation efficacy tests) described herein resulting in e.g., a greater than 4 log reduction after 28 days when the following organisms are employed: *A. brasiliensis, C. albicans, P. aeruginosa, S. aureus* and/or *E. coli* (e.g., with the initial concentrations of the organism as indicated in the experimental hereinafter); stability may be tested as described in the tests in the experimental (1 month, 2 month and 6 month stability tests under certain conditions); and the formation of co-crystals may also be tested by observation under the conditions also described in the experimental described hereinafter.

The present invention may be understood more readily by reference to the following description taken in connection with the accompanying Examples, all of which form a part of this disclosure. It is to be understood that this invention is not limited to the specific products, methods, conditions or parameters described and/or shown herein, and that the terminology used herein is for the purpose of describing particular embodiments by way of example only and is not intended to be limiting of any claimed invention. Similarly, unless otherwise stated, any description as to a possible mechanism or mode of action or reason for improvement is meant to be illustrative only, and the invention herein is not to be constrained by the correctness or incorrectness of any such suggested mechanism or mode of action or reason for improvement. Throughout this text, it is recognised that the descriptions refer both to the features and methods of making and using the formulations described herein.

When ibrutinib is referred to herein, we refer to the Compound 1 as described above, or a pharmaceutically acceptable salt thereof or a solvate thereof, for instance as described hereinbelow. Furthermore, ibrutinib (or a pharmaceutically acceptable salt or solvate thereof) is the active ingredient in the formulation of the invention and is present in a therapeutically effective amount. For example, in an aspect, where the formulation is intended for the pediatric population, 70 mg of the active ingredient ibrutinib may be present in the formulation (although there may be more mass if the ibrutinib is in the form of e.g., a salt). In an embodiment, however, in aspects of the invention, the form of ibrutinib used is not a salt or solvate form, but rather the free form.

In an aspect, the ibrutinib of the formulation of the invention is employed in its non-salt form. In another aspect, the ibrutinib employed in the formulation of the invention is the crystalline Form A as described and prepared in e.g., international patent application WO 2013/184572.

In the formulation of the invention, the active pharmaceutical ingredient, ibrutinib (or salt/solvate thereof) may be present in a suitable quantity that is therapeutically effective. The formulation of the invention encompasses a suspension and in this instance it is preferable for it to contain as much ibrutinib (or salt/solvate thereof) as can be tolerated in the presence of the pharmaceutically acceptable carrier. In an aspect, the pharmaceutically acceptable carrier (when present) is an aqueous solution and in a specific aspect it is water e.g., purified or sterilised water. However, the carrier may be selected from any of water (e.g., tap water, purified water or sterilised water), ethanol, propylene glycol, glycerol, polyethylene glycol, or the like or mixtures thereof; for instance, in one embodiment, the carrier comprises up to 90% water with the remainder being any of the other aforementioned carriers, such as ethanol, and in another embodiment, the carrier comprises at least 90% water (and the remainder, up to 10%, contains one or more of the other aforementioned carriers). In a further aspect, the quantity of ibrutinib may be present in an amount that is between 1% and 20% w/v, for instance between about 2% and 15% w/v, and, in an embodiment it may be present in between about 3% and 10% w/v, e.g., about 7% w/v and, where this relates to a formulation that is a suspension the carrier (e.g., purified water) is contemplated within the w/v ratio, and, where it relates to a formulation that is for reconstitution (e.g., a powder), the w/v ratio takes into account the volume of carrier (or liquid, e.g., water) that is intended to be (or will be) added. Hence, in an embodiment, ibrutinib (or salt/solvate thereof) is present in an amount that is between about 20 mg/ml and 150 mg/ml, in a further embodiment between about 30 mg/ml and 100 mg/ml, between about 60 mg/ml and 80 mg/ml e.g., about 70 mg/ml.

When ratios w/v are mentioned herein, and when amounts are mentioned in mg/ml (or mg/ml, used interchangeably herein), it is understood that the volume includes, in the case where the formulation of the invention is a suspension, the carrier (e.g., purified water), and, where the formulation of the invention is for reconstitution (e.g., a powder), the w/v ratio and mg/ml includes the carrier (or liquid, e.g., water) that is intended to be (or will be) added. The carrier, or pharmaceutically acceptable carrier, may also in these instances be referred to as a diluent. The carrier may be water, and in the case of a suspension, it would be preferred to be purified water (as otherwise shelf-life may be affected) and in the case of e.g., a powder for reconstitution, it may be purified water but may also be drinking water (e.g., tap water).

It is indicated herein that at least one preservative is present in the formulation of the invention that is benzyl alcohol. Hence, one or more other preservatives may also be present, for instance selected from the list hereinbelow. However, in an embodiment the preservative of the formulation of the invention comprises greater than 25%, for instance greater than 50% (by weight) benzyl alcohol and, even in this instance, the formulation may also contain other preservative ingredients other than benzyl alcohol, for instance other preservatives described hereinbelow (provided that the total percentage by weight of the other preservatives does not exceed 75% or 50%, as appropriate). In an aspect, the preservative in the formulation of the invention comprises greater than 70% benzyl alcohol, for instance greater than 90% benzyl alcohol and in an aspect, the preservative consists essentially of benzyl alcohol (i.e. the preservative of the formulation of the invention is greater than 99% or about 100% benzyl alcohol, with less than 1% or essentially no other preservatives). This is because, as will be explained hereinafter, the presence of benzyl alcohol is unexpectedly advantageous compared to other preservatives. It is extremely important for suspensions to have an adequate stability, and it remains a challenge to achieve this. However, the use of benzyl alcohol as a preservative may have advantages linked to: (i) the shelf-life of the formulation of the invention; (ii) the stability (e.g., physical stability) of the formulation and its microbiocidal activity (for instance, measured by PET—a preservation efficacy test); (iii) the reduced formation of by-products, for instance undesired co-crystals and other visible impurities or spots in the suspension, which may be caused by sedimentation or the lack of sufficient dispersion between the particles (e.g., the ibrutinib particles) in the formulation/suspension. Such visible impurities or spots are a sign of aggregates being formed, and hence a sign of instability.

As stated herein, the formulations of the invention contain one or more other preservatives in addition to benzyl alcohol (although in an aspect, the preservative is exclusively benzyl alcohol), and in this respect, the preservative may comprise one or more of antimicrobials, anti-oxidants, radical scavengers, oxygen scavengers and/or chelating agents. For instance, antimicrobials and anti-oxidants can be selected from the group consisting of benzoic acid, parabens (e.g., methyl or ethyl paraben), butylated hydroxyanisole (BHA), butylated hydroxytoluene (BHT), chlorbutol, a gallate, a hydroxybenzoate, EDTA, phenol, chlorocresol, metacresol, benzethonium chloride, myristyl-γ-piccolinium chloride, phenylmercuric acetate, thimerosal, sorbic acid and propionic acid (and propylene glycol may also be mentioned). Radical scavengers include BHA, BHT, Vitamin E and ascorbyl palmitate, and mixtures thereof. Oxygen scavengers include sodium ascorbate, sodium sulfite, L-cysteine, acetylcysteine, methionine, thioglycerol, acetone sodium bisulfite, isoascorbic acid, hydroxypropyl cyclodextrin. Chelating agents include sodium citrate, sodium EDTA and malic acid. Other preservatives that may be mentioned include acetic acid (e.g., which may act as an anti-oxidant or chelating agent) or the like. In an aspect, the other preservative is not an oxygen scavenger, and, in a further aspect, the other preservative is an antimicrobial and/or anti-oxidant. In an embodiment of the invention, the formulations of the invention do not contain a perseverative other than benzyl alcohol.

For instance, the quantity of preservative may be present in an amount that is between 0.1% and 10% w/v, for instance between about 0.1% and 5% w/v, and, in an embodiment it may be present in between about 0.5% and 2% w/v, e.g., about 1% w/v. Hence, in an embodiment, preservative is present in an amount that is between about 1 mg/ml and 50 mg/ml, in a further embodiment between about 2 mg/ml and 25 mg/ml, between about 5 mg/ml and 20 mg/ml e.g., about 10 mg/ml. As indicated herein, the formulation of the invention contains a preservative that is benzyl alcohol, and in an embodiment it contains at least about 0.1% w/v or at least about 1 mg/ml benzyl alcohol, and, in a further embodiment it contains at least about 0.5% w/v or at least about 5 mg/ml benzyl alcohol. For instance, where it is stated herein that the preservative comprises greater than 50% of benzyl alcohol, this specifically translates, where there is 1% w/v preservative, to 0.5% w/v benzyl alcohol plus 0.5% w/v of one or more other preservatives (for instance as mentioned hereinbefore). However, as it is indicated that the preservative, in an aspect, consists essentially of benzyl alcohol, then the ranges mentioned hereinbefore apply specifically to the amount of benzyl alcohol present (e.g., between about 0.5% and 2% w/v or between about 5 mg/ml and 20 mg/ml of benzyl alcohol) and, in this aspect, there are substantially no other preservatives present in the formulation of the invention.

As indicated, the formulation of the invention may be a suspension. Thus, in an aspect, the formulation of the invention comprises a further excipient that is a suspending agent. A suspending agent may be any substance that promotes particle suspension or dispersion and/or reduces sedimentation or the accumulation (or aggregation) of particles at points within the suspension. The suspending agent may also increase viscosity and promote sufficient surface activity (for instance, when it is also a wetting agent). In this respect, the suspending agent may be one or more of the following agents: alginates, a cellulose ether, methyl cellulose, hydroxyethylcellulose, carboxymethylcellulose, sodium carboxymethylcellulose, microcrystalline cellulose, acacia, tragacanth, xanthan gum, bentonite, carbomer, carrageenan, powdered cellulose and gelatin. Other suspending agents that may be mentioned include hydroxypropyl methylcellulose (HPMC) and hydroxypropyl cellulose (HPC); such agents may serve as suspending agent and wetting agent—however, in an embodiment where the wetting agent is selected from HPMC and/or HPC, the suspending agent is not the same.

In an aspect, the suspending agent that may be employed in the formulations of the invention include a carrageenan, a xanthan (or xanthan gum; for instance, any suitable polysaccharide that is produced by fermentation of carbohydrates by a gram-negative bacterium) or a cellulose ether (for instance any suitable cellulose ether, usually made by etherification of alkali cellulose). In an aspect, there is provided a formulation of the invention where the suspending agent is a cellulose ether, for instance microcrystalline cellulose and/or carboxymethylcellulose sodium (e.g., the suspending agent available under the tradename Avicel®) and may be selected based on suitability for use in suspensions where shelf-life stability is desired. The skilled person will appreciate that where microcrystalline cellulose and/or carboxymethylcellulose sodium are employed as the suspending agent, the most appropriate form will be preferred, for instance, in an embodiment, the formulation of the invention may be a reconstitutable suspension or in another embodiment the formulation may already contain a pharmaceutically acceptable carrier (e.g., purified water) and in each of these cases there may be more suitable Avicel® products for each embodiment.

In some embodiments, the suspending agent is selected from the group consisting of natural starch, a pregelatinized starch, a sodium starch, methylcrystalline cellulose, methylcellulose (e.g., Methocel®), croscarmellose, croscarmellose sodium, cross-linked sodium carboxymethylcellulose, cross-linked carboxymethylcellulose, cross-linked croscarmellose, cross-linked starch such as sodium starch glycolate, cross-linked polymer such as crospovidone, cross-linked polyvinylpyrrolidone, sodium alginate, a clay, and a gum. In an embodiment, starch is not employed as the suspending agent, as it may overly increase viscosity beyond what is desired.

The microcrystalline cellulose that may be employed as a suspending agent in the formulations of the invention may be from any suitable source, for example it may be silicified microcrystalline cellulose (SMCC) such as SMCC HD90 (e.g., PROSOLV SMCC®, which may be available through JRS Pharma), or it may be a mixture of microcrystalline cellulose and carboxymethylcellulose sodium (e.g., as marketed under the tradename Avicel®).

The quantity of suspending agent may be present in an amount that is between 0.1% and 10% w/v, for instance between about 0.1% and 5% w/v, and, in an embodiment it may be present in between about 0.5% and 2% w/v, e.g., about 1.2% w/v. Hence, in an embodiment, suspending agent is present in an amount that is between about 1 mg/ml and 50 mg/ml, in a further embodiment between about 2 mg/ml and 25 mg/ml, between about 5 mg/ml and 20 mg/ml e.g., about 12 mg/ml. In an embodiment, the suspending agent is an essential component of the formulation of the invention.

The formulation of the invention may also contain other excipients or carriers. For instance, in an aspect, the formulation of the invention may also contain a wetting agent or surfactant and representative examples include those that decrease surface tension such as those selected from the following list: gelatin, casein, lecithin, salts of negatively charged phospholipids or the acid form thereof (such as phosphatidyl glycerol, phosphatidyl inosite, phosphatidyl serine, phosphatic acid, and their salts such as alkali metal salts, e.g., their sodium salts, for example egg phosphatidyl glycerol sodium, such as the product available under the tradename Lipoid™ EPG), gum acacia, stearic acid, benzalkonium chloride, polyoxyethylene alkyl ethers, e.g., macrogol ethers such as cetomacrogol 1000, polyoxyethylene castor oil derivatives; polyoxyethylene stearates, colloidal silicon dioxide, sodium dodecylsulfate, carboxymethylcellulose sodium, bile salts such as sodium taurocholate, sodium desoxytaurocholate, sodium desoxycholate; methylcellulose, hydroxyethylcellulose, hydroxypropylcellulose, hydroxypropylmethylcellulose, magnesium aluminate silicate, polyvinyl alcohol (PVA), poloxamers, such as Pluronic™ F68, F108 and F127 which are block copolymers of ethylene oxide and propylene oxide; tyloxapol; Vitamin E-TGPS (α-tocopheryl polyethylene glycol succinate, in particular α-tocopheryl polyethylene glycol 1000 succinate); poloxamines, such as Tetronic™ 908 (T908) which is a tetrafunctional block copolymer derived from sequential addition of ethylene oxide and propylene oxide to ethylenediamine; dextran; lecithin; dioctyl ester of sodium sulfosuccinic acid such as the products sold under the tradename Aerosol OT™ (AOT); sodium lauryl sulfate (Duponol™ P); alkyl aryl polyether sulfonate available under the tradename Triton™ X-200; polyoxyethylene sorbitan fatty acid esters (Tweens™ 20, 40, 60 and 80); sorbitan esters of fatty acids (Span™ 20, 40, 60 and 80 or Arlacel™ 20, 40, 60 and 80); polyethylene glycols (such as those sold under the tradename Carbowax™ 3550 and 934); sucrose stearate and sucrose distearate mixtures such as the product available under the tradename Crodesta™ F110 or Crodesta™ SL-40; hexyldecyl trimethyl ammonium chloride (CTAC); polyvinylpyrrolidone (PVP); nonionic surfactants such as polyethoxylated castor oil (e.g., marketed under the tradename Kolliphor). If desired, two or more wetting agents and/or surfactants can be used in combination.

In an aspect, the wetting agent or surfactant is a water-soluble polymer, for instance derived from cellulose e.g., a cellulose ether such as hydroxypropylcellulose (HPC, including various marketed products) or hydroxypropylmethylcellulose (for instance the marketed product HPMC 2208). As indicated above, the suspending agent may overlap with the wetting agent and in this respect, in an aspect, the wetting agent (when present) is different to the surfactant. Hence, if the suspending agent and wetting agent are both cellulose ethers, then in an embodiment, they are different cellulose ethers (e.g., the suspending agent may be microcrystalline cellulose and/or carboxymethylcellulose sodium and the wetting agent may be HPMC).

In an aspect, there is a surfactant/wetting agent present in the formulation of the invention. The quantity of such agent may be present in an amount that is between 0.05% and 10% w/v or 0.05% and 5% w/v (e.g., 0.05% and 2% w/v), for instance between about 0.05% and 1% w/v, and, in an embodiment it may be present in between about 0.1% and 0.5% w/v, e.g., about 0.25% w/v. Hence, in an embodiment, surfactant/wetting agent is present in an amount that is between about 0.5 mg/ml and 100 mg/ml or 0.5 mg/ml and 50 mg/ml (e.g., 0.5 mg/ml and 20 mg/ml), in a further embodiment between about 0.5 mg/ml and 10 mg/ml, between about 1 mg/ml and 5 mg/ml e.g., about 2.5 mg/ml. In an embodiment, the wetting agent (or surfactant) is an essential component of the formulation of the invention.

In an embodiment, the formulation of the invention may optionally contain one or more buffering agents and/or pH adjusting agents. This is because in an aspect of the invention, the pH of the formulation of the invention is preferably in the range of about pH 4 to pH 8 (e.g., pH 5 to pH 7) and in particular about pH 6. Buffers or buffering agents are typically mixtures of two components, for instance a weak acid and its conjugate base or a weak base and its conjugate acid. For instance, in this context, components of buffers or buffering agents that may be used include salts of weak acids, and in an aspect the buffering agents may contain citric acid (such as citric acid.H$_2$O; this may be pre-formed or formed during the process to prepare the formulation of the invention) and sodium hydrogen phosphate (for instance, disodium hydrogen phosphate or monosodium dihydrogen phosphate, Na$_2$HPO$_4$ or NaH$_2$PO$_4$, respectively) and, in an aspect, the pH adjusting agents may be strong acids or strong bases such as sodium hydroxide (NaOH) and/or hydrochloric acid (HCl). Hence, examples of components of buffering agents (buffers) and pH adjusting agents include one or more of tartaric acid, maleic acid, glycine, sodium lactate/lactic acid, ascorbic acid, sodium citrates/citric acid, sodium acetate/acetic acid, sodium bicarbonate/carbonic acid, sodium succinate/succinic acid, sodium benzoate/benzoic acid, sodium phosphates, tris(hydroxymethyl)aminomethane, sodium bicarbonate/sodium carbonate, ammonium hydroxide, benzene sulfonic acid, benzoate sodium/acid, diethanolamine, glucono delta lactone, hydrochloric acid, hydrogen bromide, lysine, methanesulfonic acid, monoethanolamine, sodium hydroxide, tromethamine, gluconic, glyceric, gluratic, glutamic, ethylene diamine tetraacetic (EDTA), triethanolamine, including mixtures thereof. In an embodiment, the formulations of the invention include buffering agents containing components such as weak acids or preferably inorganic salts of acids e.g., citric acid and/or a phosphate (e.g., sodium hydrogen phosphate, such as NaH$_2$PO$_4$ or preferably Na$_2$HPO$_4$). Where citric acid is mentioned herein in the context of a component of a buffer/buffering agent, citric acid hydrate is referred to, i.e. a 1:1 ratio of citric acid and water (citric acid.H$_2$O)—as otherwise citric acid itself is hygroscopic.

In an aspect, the total amount of buffer (or buffering agents) present in the formulation of the invention is in an amount that is between 0.05% and 2% w/v, for instance between about 0.05% and 1% w/v, and, in an embodiment it may be present in between about 0.1% and 0.5% w/v, e.g., about 0.2% w/v. Hence, in an embodiment, buffering agents are present in an amount that is between about 0.5 mg/ml and 20 mg/ml, in a further embodiment between about 0.5 mg/ml and 10 mg/ml, between about 1 mg/ml and 5 mg/ml e.g., about 2 mg/ml (or between about 2 mmol/ml and 150 mmol/ml, e.g., between 5 mmol/ml and 30 mmol/ml, such as about 15 mmol/ml; whereby when citric acid hydrate and Na$_2$HPO$_4$ is employed the quantities may be about 3-4 mmol/ml and 9-11 mmol/ml, respectively). In an embodiment, the buffering agent (or mixture containing more than one buffering agent) is an essential component of the formulation of the invention, and in an aspect it comprises citric acid (citric acid.H$_2$O) and a sodium phosphate (e.g., sodium hydrogen phosphate Na$_2$HPO$_4$) for instance in a ratio, relative to mg/ml, of between 1:3 and 3:1 (e.g., between about 1:2 and 2:1, such as about 1:1) although it is preferred that the ratio is about 1:2 (as indicated relative to the mg/ml; conversion to molar ratios can also be determined accordingly—for instance, relative to mmol/ml, the ratio may be between 1:5 and 1:1 for instance between about 1:4 and 1:2, e.g., about 1:3). Thereafter, the formulation of the invention may also include acids and bases for pH adjustment purposes e.g., a strong acid and/or a strong base pH adjusting agent as mentioned hereinbefore; for instance NaOH and/or HCl may be added to the formulation of the invention q.s. for the desired pH (e.g., pH 6.0±0.1). Purified water may also be added for this purpose and is also present as the pharmaceutically acceptable carrier (or solvent) and is added q.s. based on the w/v ratios provided herein.

In an aspect, the formulation of the invention may optionally contain a sweetener. Sweeteners such as natural or artificial sweeteners, or a combination thereof, may be included in the formulations described herein. In one embodiment, the natural sweetener is sucrose including raw sugar, granulated sugar, brown sugar, confectioner's sugar, and turbinado sugar, fructose, honey, fruit sugar, high fructose corn syrup, corn syrup, sugar alcohols such as mannitol, sorbitol, xylitol, erythritol, hydrogenated starch hydrolysate, lactitol, or maltitol, osmalt, dextrose, invert sugar, agave nectar, glucose, lactose, maltose, maple sugar, date sugar, molasses, stevia extract, tagatose, trehalose, or any combinations thereof. Another embodiment, the artificial sweetener is sucralose, aspartame, saccharine, neotame, advantame, or acesulfame potassium. In still a further embodiment, the sweetener is sucralose.

When sweetener is present in the formulation of the invention, then the total amount present is in an amount that is between 0.01% and 1% w/v, for instance between about 0.05% and 0.5% w/v, and, in an embodiment it may be present in between about 0.05% and 0.2% w/v, e.g., about 0.1% w/v. Hence, in an embodiment, sweetener is present in an amount that is between about 0.1 mg/ml and 10 mg/ml, in a further embodiment between about 0.5 mg/ml and 5 mg/ml, between about 0.5 mg/ml and 2 mg/ml e.g., about 1 mg/ml.

The quantities of each of the components of the formulation of the invention may be in a specific proportion as specified below:
  Ibrutinib—70 mg/ml
  Benzyl alcohol preservative—10 mg/ml
  Suspending agent—12 mg/ml
  Wetting agent—2.5 mg/ml
  Buffers—2.1 mg/ml
  Sweetener—1 mg/ml
  pH adjusting agents (e.g., NaOH and/or HCl), q.s., ad pH 6.0±0.1
  Pharmaceutical carrier—purified water, q.s. ad 1 ml The formulations of the invention are a suspension and hence have a pharmaceutically acceptable carrier that is, in an aspect, purified water. The quantities of components of the formulation are indicated herein as being relative (w/v) to 1 ml of carrier (purified water). Hence a predetermined volume of the suspension may be used in order to administer a certain dose. In this respect, the suspensions may be more dilute or more concentrated. When the suspensions are more dilute, the relative quantities (w/v) of the active ingredient may change such that they are halved, e.g., 70 mg of ibrutinib may be present in 2 ml of purified water, or 35 mg in 1 ml). In this instance, the remaining components may also be adjusted accordingly, but preferably, they remain the same, i.e. for any remaining components (if/when present) such as benzyl alcohol, suspending agent, wetting agent, buffers, sweetener and pH adjusting agents, those quantities (in mg/ml or w/v) mentioned herein in respect of the formulations of the invention when measured relative to 1 ml of carrier (e.g., purified water) would also apply here (e.g., 10 mg/ml benzyl alcohol per ml of carrier, etc.). In such instances where there is 35 mg API (ibrutinib) per ml, if a 70 mg dose is desired, then 2 ml will be the predetermined volume of suspension (given that per ml, there is 35 mg of ibrutinib, etc.). The suspensions may also be more concentrated, in which case the relative quantities of API (ibrutinib) may change such that they are doubled, e.g., 140 mg ibrutinib per 1 ml of purified water, in which case, in the event of a 70 mg dose, 0.5 ml will be the predetermined volume. When suspensions are more concentrated, again the remaining components may also be adjusted accordingly, but preferably, they remain the same, i.e. for any remaining components (if/when present) such as benzyl alcohol, suspending agent, wetting agent, buffers, sweetener and pH adjusting agents, those quantities (in mg/ml or w/v) mentioned herein in respect of the formulations of the invention when measured relative to 1 ml of carrier (e.g., purified water) would also apply here. Hence, the formulations of the invention, or suspensions, may be more dilute or more concentrated and the predetermined volume of the formulation/suspension will therefore be adjusted accordingly. In this respect, the formulations of the invention may be adjusted with respect to the API (ibrutinib) present, which in 1 ml of carrier could range from 7 mg/ml to 700 mg/ml or be in any of the other ranges mentioned herein (e.g., 20-200 mg/ml, etc.).

Although the w/v is described herein (generally related to the weight of the component relative to the volume of the carrier e.g., the volume of the purified water), it will also be understood that the invention described herein can also be described with respect to the relative weights of each of the components of the formulations/suspensions described herein relative to each other. In such instances, the pharmaceutically-acceptable carrier (e.g., purified water) can be present in a range of volumes by weight of the components, for instance it can be 1 ml per 70 mg of ibrutinib (as described herein as specific embodiments) but equally it may be any other feasible dilutions, for instance between 1 ml per 10 mg of ibrutinib and 1 ml per 210 mg ibrutinib (e.g., between 1 ml per 35 mg of ibrutinib and 1 ml per 140 mg of ibrutinib). In such instances, the quantities of all the other components of the formulations/suspensions of the invention will also be adjusted accordingly. For instance, in an aspect, there are provided formulations of the invention where the relative quantities (w/w) of the components (in relation to each other) and compared to 70 mg of ibrutinib are as follows:
  benzyl alcohol preservative 5-15 mg;
  suspending agent 6-18 mg;
  optionally, wetting agent e.g., 1-5 mg;
  optionally, buffers e.g., 1-3 mg;
  optionally, sweetener e.g., 0.2-2 mg; and
  optionally, pH adjusting agents (q.s.)
  and wherein a pharmaceutically acceptable carrier (e.g., purified water) is present in a predetermined amount as described herein (e.g., between 1 ml per 10 mg of ibrutinib and between 1 ml per 210 mg ibrutinib, such as about 1 ml per 70 mg ibrutinib). In these cases, the suspending agent, wetting agent, buffers, sweeteners and pH adjusting agents may be any of those (e.g., the specific ones) described herein in aspects of the invention. In this respect, the following formulation is an aspect of the invention, where the relative quantities (w/w) of the components compared to 70 mg of ibrutinib are as follows:

benzyl alcohol preservative 8-12 mg;

mixture of microcrystalline cellulose and carboxymethylcellulose sodium (e.g., Avicel®) 10-14 mg;

optionally, hydroxypropylmethylcellulose (HPMC) 2-3 mg;

optionally, citric acid.H$_2$O and/or phosphate such as sodium hydrogen phosphate 1.5-2.5 mg;

optionally, sucralose 0.5-1.5 mg;

and, optionally, NaOH and/or HCl (q.s.) in order to adjust pH and wherein, as indicated above, a pharmaceutically acceptable carrier (e.g., purified water) is present in a predetermined amount as described herein (e.g., between 1 ml per 10 mg of ibrutinib and between 1 ml per 210 mg ibrutinib, such as about 1 ml per 70 mg ibrutinib).

As described herein, the formulations of the invention contain a pharmaceutical carrier such as purified water. Hence, doses will be administered as a volume of the suspension. In the case described herein, if a dose is 70 mg of ibrutinib, then the amount of carrier (e.g., purified water) is 1 ml. As indicated herein, the suspension may be more dilute or more concentrated but in any case the volume of the suspension required for a certain dose will be predetermined.

In further aspects of the invention, the components of the formulation of the invention may be, based on the pharmaceutical carrier being 1 ml of purified water, any one of the following proportions:

ibrutinib 20-200 mg/ml; benzyl alcohol preservative 2.5-25 mg/ml; suspending agent 2-24 mg/ml; optionally, wetting agent e.g., 0.5-10 mg/ml; optionally, buffers e.g., 0.5-10 mg/ml; optionally, sweetener e.g., 0.1-5 mg/ml; and, optionally, pH adjusting agents (q.s.);

ibrutinib 40-100 mg/ml; benzyl alcohol preservative 5-15 mg/ml; suspending agent 6-18 mg/ml; optionally, wetting agent e.g., 1-5 mg/ml; optionally, buffers e.g., 1-3 mg/ml; optionally, sweetener e.g., 0.2-2 mg/ml; and, optionally, pH adjusting agents (q.s.); or ibrutinib 60-80 mg/ml; benzyl alcohol preservative 8-12 mg/ml; suspending agent 10-14 mg/ml; optionally, wetting agent e.g., 2-3 mg/ml; optionally, buffers e.g., 1.5-2.5 mg/ml; optionally, sweetener e.g., 0.5-1.5 mg/ml; and, optionally, pH adjusting agents (q.s.).

In certain embodiments, formulations of the invention will have components specified (for instance as described in aspects of the invention hereinbefore), for instance: the suspending agent is a mixture of microcrystalline cellulose and carboxymethylcellulose sodium (e.g., as marketed under the tradename Avicel® e.g., Avicel® RC-591);

the wetting agent is hydroxypropylmethylcellulose (HPMC);

the buffer is citric acid.H$_2$O and/or phosphate such as sodium hydrogen phosphate (e.g., a mixture of the two in a ratio as described herein);

the sweetener is sucralose; and/or the pH adjusting agents are NaOH and HCl.

And hence in specific aspects of the invention, the following formulations of the invention are included:

ibrutinib 60-80 mg/ml;

benzyl alcohol preservative 8-12 mg/ml;

mixture of microcrystalline cellulose and carboxymethylcellulose sodium (e.g., Avicel®) 10-14 mg/ml;

optionally, hydroxypropylmethylcellulose (HPMC) 2-3 mg/ml;

optionally, citric acid.H$_2$O and/or phosphate such as sodium hydrogen phosphate 1.5-2.5 mg/ml;

optionally, sucralose 0.5-1.5 mg/ml;

and, optionally, NaOH and/or HCl (q.s.) in order to adjust pH.

In an embodiment, the formulations of the invention also contain a wetting agent (e.g., HPMC; for instance in the quantities described herein). In an embodiment, the formulations also contain buffers (e.g., citric acid.H$_2$O and/or sodium hydrogen phosphate; for instance in the quantities described herein). In an embodiment, the formulations also contain a sweetener (e.g., sucralose; for instance in the quantities mentioned herein). In an embodiment, NaOH and/or HCl are added to the formulations of the invention in order to adjust pH. The pH may be within any suitable range that permits (or preserves) adequate shelf-life of the formulation, which is particularly important for suspensions, and a key reason why the choice of preservative is important. To achieve the desired pH, appropriate adjusting with e.g., NaOH and/or HCl may be undertaken. In an aspect, the pH of the formulation/suspension of the invention is between about pH 3 and pH 9, but in a further embodiment, the pH is between about pH 4 and pH 8 (for instance between about pH 5 and pH 7, e.g., between about pH 5.5 and pH 6.5). In an aspect, the pH of the formulations/suspensions described herein are adjusted to be about pH 6.

It is indicated herein that a key aspect of the invention is the presence of benzyl alcohol as a preservative. This is because, as described herein, including in the examples and testing conducted, benzyl alcohol was the most suitable preservative. For instance, co-crystallisation with the API (ibrutinib) was exceptionally not observed.

The formulations/suspensions of the invention, are those in which the particle size distribution (PSD) remains within certain thresholds. The formulations/suspensions of the invention may also be advantageous compared to others in view of the PSD remaining within a certain threshold over time and under certain stressed conditions (e.g., temperature and other different storage conditions).

In an embodiment, suitable agitation is employed in the process for preparing a suspension described herein to ensure that the API (ibrutinib) is evenly dispersed throughout the pharmaceutically acceptable carrier (e.g., purified water). By evenly dispersed, we mean that the API particles (i.e. ibrutinib particles) are dispersed, or spread out/distributed, throughout the carrier (e.g., water) of the suspension, for instance after shaking (or light shaking) as without shaking the suspension may have a gel-like texture. This results in any equal portion of the carrier (e.g., water) containing approximately equal amounts of the API (ibrutinib) particles (by weight), by which we mean within a deviation of ±25%, preferably ±15%, and especially ±10% (or less e.g., within ±5%). Hence, if 700 mg of ibrutinib is dispersed in 10 ml of water, then each portion of 2.5 ml of water (when divided) should contain about 175 mg of ibrutinib, but with a possible deviation of ±25% (i.e. ±43.75 mg), preferably, ±15% (i.e. ±26.25 mg) and especially ±10% (i.e. ±17.5 mg)—most preferably the deviation will be ±5% (i.e. ±8.75 mg). Hence, the suspension is physically substantially uniform or homogenous throughout the carrier (e.g., water medium) in which it is placed (after the necessary time for dispersion; see above, e.g., through agitation). It may be the case that the larger the volume of water per mg of active ingredient, the less deviation there may be in terms of dispersion.

The formulations of the invention may also have active ingredient (API), i.e. ibrutinib, having a certain particle size and for there to be a certain particle size distribution (PSD). For instance, $d_v^{50}$ is, in an embodiment, less than 100 µm, for instance less than µm.

Further, in the context of the invention, in certain embodiments:

$d_v^{10}$ is less than 5 µm (preferably less than 2 µm, for instance less than 1.5 µm, e.g., around 1.0 or 1.1 µm (or even less)

$d_v^{50}$ is less than 10 µm (preferably less than 8 µm, for instance less than 6 µm, e.g., around 4-5 µm (or even less)

$d_v^{90}$ is less than 20 µm (preferably less than 15 µm, for instance less than 10 µm, e.g., around 8-9 µm (or even less)

As used herein, the term $d^{50}$ (or $d_v^{50}$) has its conventional meaning as known to the person skilled in the art and can be measured by art-known particle size measuring techniques such as, for example, sedimentation field flow fractionation, photon correlation spectroscopy, laser diffraction or disk centrifugation. The $d_v^{50}$ mentioned herein may be related to volume distributions of the particles. In that instance, by "a $d_v^{50}$ of 5 µm" it is meant that at least 50% of the volume of the particles has a particle size of less than 5 µm. The same applies to the other particle sizes mentioned and $d_v^{10}$ and $d_v^{90}$ have analogous meanings. Usually volume and weight distribution result in the same or about the same value for the average particle size.

In the context of the invention, the formulations (e.g., suspensions) of the invention described herein may have the advantage that particle size distribution (PSD) remains optimal, thus not impacting on the quality of the product.

It is to be appreciated that there is overlap between the additives (excipients/diluents etc.) used in the formulations (e.g., suspensions) described herein, since a given additive is often classified differently by different practitioners in the field, or is commonly used for any of several different functions. Thus, the additives mentioned herein should be taken as merely exemplary, and not limiting, of the types of additives that can be included in formulations described herein. The amounts of such additives can be readily determined by one skilled in the art, according to the particular properties desired.

In another aspect is a method of treating a disease in a patient in need of such treatment, comprising administering to the patient a therapeutically effective amount of a pharmaceutical composition or formulation described herein.

In another aspect is a method of treating hematological malignancy in a patient in need of such treatment, comprising administering to the patient a therapeutically effective amount of a pharmaceutical composition or formulation described herein. In some embodiments, the cancer is a B-cell proliferative disorder. In some embodiments, the B-cell proliferative disorder is diffuse large B cell lymphoma, follicular lymphoma or chronic lymphocytic leukemia. In some embodiments, the cancer is a B cell malignancy. In some embodiments, the cancer is a B cell malignancy selected from chronic lymphocytic leukemia (CLL)/small lymphocytic lymphoma (SLL), mantle cell lymphoma (MCL), diffuse large B Cell lymphoma (DLBCL), and multiple myeloma. In some embodiments, the cancer is a lymphoma or leukemia. In some embodiments, the cancer is diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, or lymphomatoid granulomatosis.

In another aspect is a process for preparing a pharmaceutical composition or formulation (e.g., as described herein) comprising ibrutinib, the process comprising preparing bringing the components of the composition/formulation into association with each other. In an aspect, the requisite preservative that is benzyl alcohol is added first, followed by the other components of the composition/formulation of the invention (e.g., the carrier, ibrutinib and suspending agent, etc.), and, in a further specific aspect, the composition/formulation may be prepared as described in the examples hereinafter.

In another aspect, provided herein are methods for treating a patient by administering formulations (e.g., suspensions) described herein containing Compound 1.

Other objects, features and advantages of the methods and compositions/formulations described herein will become apparent from the following detailed description. It should be understood, however, that the detailed description and the specific examples, while indicating specific embodiments, are given by way of illustration only, since various changes and modifications within the spirit and scope of the present disclosure will become apparent to those skilled in the art from this detailed description. The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

INCORPORATION BY REFERENCE

All publications and patent applications mentioned in this specification are herein incorporated by reference to the extent applicable and relevant.

DETAILED DESCRIPTION OF THE INVENTION

In some embodiments, the methods described herein can be used to treat a cancer, e.g., B-cell proliferative disorders, which include, but are not limited to diffuse large B cell lymphoma, follicular lymphoma, chronic lymphocytic lymphoma, chronic lymphocytic leukemia, B-cell prolymphocytic leukemia, lymphoplasmacytic lymphoma/Waldenstrom macroglobulinemia, splenic marginal zone lymphoma, plasma cell myeloma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, burkitt lymphoma/leukemia, and lymphomatoid granulomatosis.

Hematological Malignancies

Disclosed herein, in certain embodiments, is a method for treating a hematological malignancy in an individual in need thereof, comprising: administering to the individual a formulation (e.g., suspension) described herein comprising an amount of Compound 1.

In some embodiments, the hematological malignancy is a non-Hodgkin's lymphoma (NHL). In some embodiments, the hematological malignancy is a chronic lymphocytic leukemia (CLL), small lymphocytic lymphoma (SLL), high risk CLL, or a non-CLL/SLL lymphoma. In some embodiments, the hematological malignancy is follicular lymphoma (FL), diffuse large B-cell lymphoma (DLBCL), mantle cell lymphoma (MCL), Waldenstrom's macroglobulinemia, multiple myeloma (MM), marginal zone lymphoma, Burkitt's lymphoma, non-Burkitt high grade B cell lymphoma, or extranodal marginal zone B cell lymphoma. In some embodiments, the hematological malignancy is acute or chronic myelogenous (or myeloid) leukemia, myelodysplastic syndrome, acute lymphoblastic leukemia, or precursor B-cell acute lymphoblastic leukemia. In some embodiments, the hematological malignancy is chronic lymphocytic leukemia (CLL). In some embodiments, the hematological malignancy is mantle cell lymphoma (MCL). In some embodiments, the hematological malignancy is diffuse large B-cell lymphoma (DLBCL). In some embodiments, the hematological malignancy is diffuse large B-cell lymphoma (DLBCL), ABC subtype. In some embodiments, the hematological malignancy is diffuse large B-cell lymphoma (DLBCL), GCB subtype. In some embodiments, the hematological malignancy is Waldenstrom's macroglobulinemia (WM). In some embodiments, the hematological malignancy is multiple myeloma (MM). In some embodiments, the hematological malignancy is Burkitt's lymphoma. In some embodiments, the hematological malignancy is follicular lymphoma (FL). In some embodiments, the hematological malignancy is transformed follicular lymphoma. In some embodiments, the hematological malignancy is marginal zone lymphoma.

In some embodiments, the hematological malignancy is relapsed or refractory non-Hodgkin's lymphoma (NHL). In some embodiments, the hematological malignancy is relapsed or refractory diffuse large B-cell lymphoma (DLBCL), relapsed or refractory mantle cell lymphoma (MCL), relapsed or refractory follicular lymphoma (FL), relapsed or refractory CLL, relapsed or refractory SLL, relapsed or refractory multiple myeloma, relapsed or refractory Waldenstrom's macroglobulinemia, relapsed or refractory multiple myeloma (MM), relapsed or refractory marginal zone lymphoma, relapsed or refractory Burkitt's lymphoma, relapsed or refractory non-Burkitt high grade B cell lymphoma, relapsed or refractory extranodal marginal zone B cell lymphoma. In some embodiments, the hematological malignancy is a relapsed or refractory acute or chronic myelogenous (or myeloid) leukemia, relapsed or refractory myelodysplastic syndrome, relapsed or refractory acute lymphoblastic leukemia, or relapsed or refractory precursor B-cell acute lymphoblastic leukemia. In some embodiments, the hematological malignancy is relapsed or refractory chronic lymphocytic leukemia (CLL). In some embodiments, the hematological malignancy is relapsed or refractory mantle cell lymphoma (MCL). In some embodiments, the hematological malignancy is relapsed or refractory diffuse large B-cell lymphoma (DLBCL). In some embodiments, the hematological malignancy is relapsed or refractory diffuse large B-cell lymphoma (DLBCL), ABC subtype. In some embodiments, the hematological malignancy is relapsed or refractory diffuse large B-cell lymphoma (DLBCL), GCB subtype. In some embodiments, the hematological malignancy is relapsed or refractory Waldenstrom's macroglobulinemia (WM). In some embodiments, the hematological malignancy is relapsed or refractory multiple myeloma (MM). In some embodiments, the hematological malignancy is relapsed or refractory Burkitt's lymphoma. In some embodiments, the hematological malignancy is relapsed or refractory follicular lymphoma (FL).

In some embodiments, the hematological malignancy is a hematological malignancy that is classified as high-risk. In some embodiments, the hematological malignancy is high risk CLL or high risk SLL.

B-cell lymphoproliferative disorders (BCLDs) are neoplasms of the blood and encompass, inter alia, non-Hodgkin lymphoma, multiple myeloma, and leukemia. BCLDs can originate either in the lymphatic tissues (as in the case of lymphoma) or in the bone marrow (as in the case of leukemia and myeloma), and they all are involved with the uncontrolled growth of lymphocytes or white blood cells. There are many subtypes of BCLD, e.g., chronic lymphocytic leukemia (CLL) and non-Hodgkin lymphoma (NHL). The disease course and treatment of BCLD is dependent on the BCLD subtype; however, even within each subtype the clinical presentation, morphologic appearance, and response to therapy is heterogeneous.

Malignant lymphomas are neoplastic transformations of cells that reside predominantly within lymphoid tissues. Two groups of malignant lymphomas are Hodgkin's lymphoma and non-Hodgkin's lymphoma (NHL). Both types of lymphomas infiltrate reticuloendothelial tissues. However, they differ in the neoplastic cell of origin, site of disease, presence of systemic symptoms, and response to treatment (Freedman et al., "Non-Hodgkin's Lymphomas" Chapter 134, Cancer Medicine, (an approved publication of the American Cancer Society, B.C. Decker Inc., Hamilton, Ontario, 2003).

Non-Hodgkin's Lymphomas

Disclosed herein, in certain embodiments, is a method for treating a non-Hodgkin's lymphoma in an individual in need thereof, comprising: administering to the individual a formulation (e.g., suspension) described herein comprising an amount of Compound 1.

Further disclosed herein, in certain embodiments, is a method for treating relapsed or refractory non-Hodgkin's lymphoma in an individual in need thereof, comprising: administering to the individual a therapeutically-effective amount of a formulation described herein comprising Compound 1. In some embodiments, the non-Hodgkin's lymphoma is relapsed or refractory diffuse large B-cell lymphoma (DLBCL), relapsed or refractory mantle cell lymphoma, relapsed or refractory follicular lymphoma, or relapsed or refractory CLL.

Non-Hodgkin lymphomas (NHL) are a diverse group of malignancies that are predominately of B-cell origin. NHL may develop in any organs associated with lymphatic system such as spleen, lymph nodes or tonsils and can occur at any age. NHL is often marked by enlarged lymph nodes, fever, and weight loss. NHL is classified as either B-cell or T-cell NHL. Lymphomas related to lymphoproliferative disorders following bone marrow or stem cell transplantation are usually B-cell NHL. In the Working Formulation classification scheme, NHL has been divided into low-, intermediate-, and high-grade categories by virtue of their natural histories (see "The Non-Hodgkin's Lymphoma Pathologic Classification Project," Cancer 49(1982):2112-2135). The low-grade lymphomas are indolent, with a median survival of 5 to 10 years (Homing and Rosenberg (1984) N. Engl. J. Med. 311:1471-1475). Although chemotherapy can induce remissions in the majority of indolent lymphomas, cures are rare and most patients eventually relapse, requiring further therapy. The intermediate- and high-grade lymphomas are more aggressive tumors, but they have a greater chance for cure with chemotherapy. However, a significant proportion of these patients will relapse and require further treatment.

A non-limiting list of the B-cell NHL includes Burkitt's lymphoma (e.g., Endemic Burkitt's Lymphoma and Sporadic Burkitt's Lymphoma), Cutaneous B-Cell Lymphoma, Cutaneous Marginal Zone Lymphoma (MZL), Diffuse Large Cell Lymphoma (DLBCL), Diffuse Mixed Small and Large Cell Lymphoma, Diffuse Small Cleaved Cell, Diffuse Small Lymphocytic Lymphoma, Extranodal Marginal Zone B-cell lymphoma, follicular lymphoma, Follicular Small Cleaved Cell (Grade 1), Follicular Mixed Small Cleaved and Large Cell (Grade 2), Follicular Large Cell (Grade 3), Intravascular Large B-Cell Lymphoma, Intravascular Lymphomatosis, Large Cell Immunoblastic Lymphoma, Large Cell Lymphoma (LCL), Lymphoblastic Lymphoma, MALT Lymphoma, Mantle Cell Lymphoma (MCL), immunoblastic large cell lymphoma, precursor B-lymphoblastic lymphoma, mantle cell lymphoma, chronic lymphocytic leukemia (CLL)/small lymphocytic lymphoma (SLL), extranodal marginal zone B-cell lymphoma-mucosa-associated lymphoid tissue (MALT) lymphoma, Mediastinal Large B-Cell Lymphoma, nodal marginal zone B-cell lymphoma, splenic marginal zone B-cell lymphoma, primary mediastinal B-cell lymphoma, lymphoplasmocytic lymphoma, hairy cell leukemia, Waldenstrom's Macroglobulinemia, and primary central nervous system (CNS) lymphoma. Additional non-Hodgkin's lymphomas are contemplated within the scope of the present invention and apparent to those of ordinary skill in the art.

DLBCL

Disclosed herein, in certain embodiments, is a method for treating a DLCBL in an individual in need thereof, comprising: administering to the individual a formulation (e.g., suspension) described herein comprising an amount of Compound 1. Further disclosed herein, in certain embodiments, is a method for treating relapsed or refractory DLCBL in an individual in need thereof, comprising: administering to the individual a formulation (e.g., suspension) described herein comprising a therapeutically-effective amount of Compound 1 (or administering a therapeutically-effective amount of a formulation described herein).

As used herein, the term "Diffuse large B-cell lymphoma (DLBCL)" refers to a neoplasm of the germinal center B lymphocytes with a diffuse growth pattern and a high-intermediate proliferation index. DLBCLs represent approximately 30% of all lymphomas and may present with several morphological variants including the centroblastic, immunoblastic, T-cell/histiocyte rich, anaplastic and plasmoblastic subtypes. Genetic tests have shown that there are different subtypes of DLBCL. These subtypes seem to have different outlooks (prognoses) and responses to treatment. DLBCL can affect any age group but occurs mostly in older people (the average age is mid-60s).

Disclosed herein, in certain embodiments, is a method for treating diffuse large B-cell lymphoma, activated B cell-like subtype (ABC-DLBCL), in an individual in need thereof, comprising: administering to the individual ibrutinib in an amount from 100 mg/day up to, and including, 1000 mg/day. The ABC subtype of diffuse large B-cell lymphoma (ABC-DLBCL) is thought to arise from post germinal center B cells that are arrested during plasmatic differentiation. The ABC subtype of DLBCL (ABC-DLBCL) accounts for approximately 30% total DLBCL diagnoses. It is considered the least curable of the DLBCL molecular subtypes and, as such, patients diagnosed with the ABC-DLBCL typically display significantly reduced survival rates compared with individuals with other types of DLCBL. ABC-DLBCL is most commonly associated with chromosomal translocations deregulating the germinal center master regulator BCL6 and with mutations inactivating the PRDM1 gene, which encodes a transcriptional repressor required for plasma cell differentiation.

Follicular Lymphoma

Disclosed herein, in certain embodiments, is a method for treating a follicular lymphoma in an individual in need thereof, comprising: administering to the individual a formulation (e.g., suspension) described herein comprising an amount of Compound 1. Further disclosed herein, in certain embodiments, is a method for treating relapsed or refractory follicular lymphoma in an individual in need thereof, comprising: administering to the individual a formulation (e.g., suspension) described herein comprising a therapeutically-effective amount of Compound 1 (or administering a therapeutically-effective amount of a formulation described herein).

As used herein, the term "follicular lymphoma" refers to any of several types of non-Hodgkin's lymphoma in which the lymphomatous cells are clustered into nodules or follicles. The term follicular is used because the cells tend to grow in a circular, or nodular, pattern in lymph nodes. The average age for people with this lymphoma is about 60.

CLL/SLL

Disclosed herein, in certain embodiments, is a method for treating a CLL or SLL in an individual in need thereof, comprising: administering to the individual a formulation (e.g., suspension) described herein comprising an amount of Compound 1. Further disclosed herein, in certain embodiments, is a method for treating relapsed or refractory CLL or SLL in an individual in need thereof, comprising: administering to the individual a formulation (e.g., suspension) described herein comprising a therapeutically-effective amount of Compound 1 (or administering a therapeutically-effective amount of a formulation described herein).

Chronic lymphocytic leukemia and small lymphocytic lymphoma (CLL/SLL) are commonly thought as the same disease with slightly different manifestations. Where the cancerous cells gather determines whether it is called CLL or SLL. When the cancer cells are primarily found in the lymph nodes, lima bean shaped structures of the lymphatic system (a system primarily of tiny vessels found in the body), it is called SLL. SLL accounts for about 5% to 10% of all lymphomas. When most of the cancer cells are in the bloodstream and the bone marrow, it is called CLL.

Both CLL and SLL are slow-growing diseases, although CLL, which is much more common, tends to grow slower. CLL and SLL are treated the same way. They are usually not considered curable with standard treatments, but depending on the stage and growth rate of the disease, most patients live longer than 10 years. Occasionally over time, these slow-growing lymphomas may transform into a more aggressive type of lymphoma.

Chronic lymphoid leukemia (CLL) is the most common type of leukemia. It is estimated that 100,760 people in the United States are living with or are in remission from CLL. Most (>75%) people newly diagnosed with CLL are over the age of 50. Currently CLL treatment focuses on controlling the disease and its symptoms rather than on an outright cure.

CLL is treated by chemotherapy, radiation therapy, biological therapy, or bone marrow transplantation. Symptoms are sometimes treated surgically (splenectomy removal of enlarged spleen) or by radiation therapy ("de-bulking" swollen lymph nodes). Though CLL progresses slowly in most cases, it is considered generally incurable. Certain CLLs are classified as high-risk. As used herein, "high risk CLL" means CLL characterized by at least one of the following 1) 17p13-; 2) 11q22-; 3) unmutated IgVH together with ZAP-70+ and/or CD38+; or 4) trisomy 12.

CLL treatment is typically administered when the patient's clinical symptoms or blood counts indicate that the disease has progressed to a point where it may affect the patient's quality of life.

Small lymphocytic leukemia (SLL) is very similar to CLL described supra, and is also a cancer of B-cells. In SLL the abnormal lymphocytes mainly affect the lymph nodes. However, in CLL the abnormal cells mainly affect the blood and the bone marrow. The spleen may be affected in both conditions. SLL accounts for about 1 in 25 of all cases of non-Hodgkin lymphoma. It can occur at any time from young adulthood to old age, but is rare under the age of 50. SLL is considered an indolent lymphoma. This means that the disease progresses very slowly, and patients tend to live many years after diagnosis. However, most patients are diagnosed with advanced disease, and although SLL responds well to a variety of chemotherapy drugs, it is generally considered to be incurable. Although some cancers tend to occur more often in one gender or the other, cases and deaths due to SLL are evenly split between men and women. The average age at the time of diagnosis is 60 years.

Although SLL is indolent, it is persistently progressive. The usual pattern of this disease is one of high response rates to radiation therapy and/or chemotherapy, with a period of disease remission. This is followed months or years later by an inevitable relapse. Re-treatment leads to a response again, but again the disease will relapse. This means that although the short-term prognosis of SLL is quite good, over time, many patients develop fatal complications of recurrent disease. Considering the age of the individuals typically diagnosed with CLL and SLL, there is a need in the art for a simple and effective treatment of the disease with minimum side-effects that do not impede on the patient's quality of life. The instant invention fulfills this long standing need in the art.

Mantle Cell Lymphoma

Disclosed herein, in certain embodiments, is a method for treating a Mantle cell lymphoma in an individual in need thereof, comprising: administering to the individual a formulation (e.g., suspension) described herein comprising an amount of Compound 1. Further disclosed herein, in certain embodiments, is a method for treating relapsed or refractory Mantle cell lymphoma in an individual in need thereof, comprising: administering to the individual a formulation (e.g., suspension) described herein comprising a therapeutically-effective amount of Compound 1 (or administering a therapeutically-effective amount of a formulation described herein).

As used herein, the term, "Mantle cell lymphoma" refers to a subtype of B-cell lymphoma, due to CD5 positive antigen-naive pregerminal center B-cell within the mantle zone that surrounds normal germinal center follicles. MCL cells generally over-express cyclin D1 due to a t(11:14) chromosomal translocation in the DNA. More specifically, the translocation is at t(11;14)(q13;q32). Only about 5% of lymphomas are of this type. The cells are small to medium in size. Men are affected most often. The average age of patients is in the early 60s. The lymphoma is usually widespread when it is diagnosed, involving lymph nodes, bone marrow, and, very often, the spleen. Mantle cell lymphoma is not a very fast growing lymphoma, but is difficult to treat.

Marginal Zone B-cell Lymphoma

Disclosed herein, in certain embodiments, is a method for treating a marginal zone B-cell lymphoma in an individual in need thereof, comprising: administering to the individual a formulation (e.g., suspension) described herein comprising an amount of Compound 1. Further disclosed herein, in certain embodiments, is a method for treating relapsed or refractory marginal zone B-cell lymphoma in an individual in need thereof, comprising: administering to the individual a formulation (e.g., suspension) described herein comprising a therapeutically-effective amount of Compound 1 (or administering a therapeutically-effective amount of a formulation described herein).

As used herein, the term "marginal zone B-cell lymphoma" refers to a group of related B-cell neoplasms that involve the lymphoid tissues in the marginal zone, the patchy area outside the follicular mantle zone. Marginal zone lymphomas account for about 5% to 10% of lymphomas. The cells in these lymphomas look small under the microscope. There are 3 main types of marginal zone lymphomas including extranodal marginal zone B-cell lymphomas, nodal marginal zone B-cell lymphoma, and splenic marginal zone lymphoma.

MALT

Disclosed herein, in certain embodiments, is a method for treating a MALT in an individual in need thereof, comprising: administering to the individual a formulation (e.g., suspension) described herein comprising an amount of Compound 1. Further disclosed herein, in certain embodiments, is a method for treating relapsed or refractory MALT in an individual in need thereof, comprising: administering to the individual a formulation (e.g., suspension) described herein comprising a therapeutically-effective amount of Compound 1 (or administering a therapeutically-effective amount of a formulation described herein).

The term "mucosa-associated lymphoid tissue (MALT) lymphoma", as used herein, refers to extranodal manifestations of marginal-zone lymphomas. Most MALT lymphoma are a low grade, although a minority either manifest initially as intermediate-grade non-Hodgkin lymphoma (NHL) or evolve from the low-grade form. Most of the MALT lymphoma occur in the stomach, and roughly 70% of gastric MALT lymphoma are associated with *Helicobacter pylori* infection. Several cytogenetic abnormalities have been identified, the most common being trisomy 3 or t(11;18). Many of these other MALT lymphoma have also been linked to infections with bacteria or viruses. The average age of patients with MALT lymphoma is about 60.

Nodal Marginal Zone B-Cell Lymphoma

Disclosed herein, in certain embodiments, is a method for treating a nodal marginal zone B-cell lymphoma in an individual in need thereof, comprising: administering to the individual a formulation (e.g., suspension) described herein comprising an amount of Compound 1. Further disclosed herein, in certain embodiments, is a method for treating relapsed or refractory nodal marginal zone B-cell lymphoma in an individual in need thereof, comprising: administering to the individual a formulation (e.g., suspension) described herein comprising a therapeutically-effective amount of Compound 1 (or administering a therapeutically-effective amount of a formulation described herein).

The term "nodal marginal zone B-cell lymphoma" refers to an indolent B-cell lymphoma that is found mostly in the lymph nodes. The disease is rare and only accounts for 1% of all Non-Hodgkin's Lymphomas (NHL). It is most commonly diagnosed in older patients, with women more susceptible than men. The disease is classified as a marginal zone lymphoma because the mutation occurs in the marginal zone of the B-cells. Due to its confinement in the lymph nodes, this disease is also classified as nodal.

Splenic Marginal Zone B-Cell Lymphoma

Disclosed herein, in certain embodiments, is a method for treating a splenic marginal zone B-cell lymphoma in an individual in need thereof, comprising: administering to the individual a formulation (e.g., suspension) described herein comprising an amount of Compound 1. Further disclosed herein, in certain embodiments, is a method for treating relapsed or refractory splenic marginal zone B-cell lymphoma in an individual in need thereof, comprising: administering to the individual a formulation (e.g., suspension) described herein comprising a therapeutically-effective amount of Compound 1 (or administering a therapeutically-effective amount of a formulation described herein).

The term "splenic marginal zone B-cell lymphoma" refers to specific low-grade small B-cell lymphoma that is incorporated in the World Health Organization classification. Characteristic features are splenomegaly, moderate lymphocytosis with villous morphology, intrasinusoidal pattern of involvement of various organs, especially bone marrow, and relative indolent course. Tumor progression with increase of blastic forms and aggressive behavior are observed in a minority of patients. Molecular and cytogenetic studies have shown heterogeneous results probably because of the lack of standardized diagnostic criteria.

Burkitt Lymphoma

Disclosed herein, in certain embodiments, is a method for treating a Burkitt lymphoma in an individual in need thereof, comprising: administering to the individual a formulation (e.g., suspension) described herein comprising an amount of Compound 1. Further disclosed herein, in certain embodiments, is a method for treating relapsed or refractory Burkitt lymphoma in an individual in need thereof, comprising: administering to the individual a formulation (e.g., suspension) described herein comprising a therapeutically-effective amount of Compound 1 (or administering a therapeutically-effective amount of a formulation described herein).

The term "Burkitt lymphoma" refers to a type of Non-Hodgkin Lymphoma (NHL) that commonly affects children. It is a highly aggressive type of B-cell lymphoma that often starts and involves body parts other than lymph nodes. In spite of its fast-growing nature, Burkitt's lymphoma is often curable with modem intensive therapies. There are two broad types of Burkitt's lymphoma—the sporadic and the endemic varieties: Endemic Burkitt's lymphoma: The disease involves children much more than adults, and is related to Epstein Barr Virus (EBV) infection in 95% cases. It occurs primarily is equatorial Africa, where about half of all childhood cancers are Burkitt's lymphoma. It characteristically has a high chance of involving the jawbone, a rather distinctive feature that is rare in sporadic Burkitt's. It also commonly involves the abdomen. Sporadic Burkitt's lymphoma: The type of Burkitt's lymphoma that affects the rest of the world, including Europe and the Americas is the sporadic type. Here too, it's mainly a disease in children. The link between Epstein Barr Virus (EBV) is not as strong as with the endemic variety, though direct evidence of EBV infection is present in one out of five patients. More than the involvement of lymph nodes, it is the abdomen that is notably affected in more than 90% of the children. Bone marrow involvement is more common than in the sporadic variety.

Waldenstrom Macroglobulinemia

Disclosed herein, in certain embodiments, is a method for treating a Waldenstrom macroglobulinemia in an individual in need thereof, comprising: administering to the individual a formulation (e.g., suspension) described herein comprising an amount of Compound 1. Further disclosed herein, in certain embodiments, is a method for treating relapsed or refractory Waldenstrom macroglobulinemia in an individual in need thereof, comprising: administering to the individual a formulation (e.g., suspension) described herein comprising a therapeutically-effective amount of Compound 1 (or administering a therapeutically-effective amount of a formulation described herein).

The term "Waldenstrom macroglobulinemia", also known as lymphoplasmacytic lymphoma, is cancer involving a subtype of white blood cells called lymphocytes. It is characterized by an uncontrolled clonal proliferation of terminally differentiated B lymphocytes. It is also characterized by the lymphoma cells making an antibody called immunoglobulin M (IgM). The IgM antibodies circulate in the blood in large amounts, and cause the liquid part of the blood to thicken, like syrup. This can lead to decreased blood flow to many organs, which can cause problems with vision (because of poor circulation in blood vessels in the back of the eyes) and neurological problems (such as headache, dizziness, and confusion) caused by poor blood flow within the brain. Other symptoms can include feeling tired and weak, and a tendency to bleed easily. The underlying etiology is not fully understood but a number of risk factors have been identified, including the locus 6p21.3 on chromosome 6. There is a 2- to 3-fold risk increase of developing WM in people with a personal history of autoimmune diseases with autoantibodies and particularly elevated risks associated with hepatitis, human immunodeficiency virus, and rickettsiosis.

Multiple Myeloma

Disclosed herein, in certain embodiments, is a method for treating a myeloma in an individual in need thereof, comprising: administering to the individual a formulation (e.g., suspension) described herein comprising an amount of Compound 1. Further disclosed herein, in certain embodiments, is a method for treating relapsed or refractory myeloma in an individual in need thereof, comprising: administering to the individual a formulation (e.g., suspension) described herein comprising a therapeutically-effective amount of Compound 1 (or administering a therapeutically-effective amount of a formulation described herein).

Multiple myeloma, also known as MM, myeloma, plasma cell myeloma, or as Kahler's disease (after Otto Kahler) is a cancer of the white blood cells known as plasma cells. A type of B cell, plasma cells are a crucial part of the immune system responsible for the production of antibodies in humans and other vertebrates. They are produced in the bone marrow and are transported through the lymphatic system.

Leukemia

Disclosed herein, in certain embodiments, is a method for treating a leukemia in an individual in need thereof, comprising: administering to the individual a formulation (e.g., suspension) described herein comprising an amount of Compound 1. Further disclosed herein, in certain embodiments, is a method for treating relapsed or refractory leukemia in an individual in need thereof, comprising: administering to the individual a formulation (e.g., suspension) described herein comprising a therapeutically-effective amount of Compound 1 (or administering a therapeutically-effective amount of a formulation described herein).

Leukemia is a cancer of the blood or bone marrow characterized by an abnormal increase of blood cells, usually leukocytes (white blood cells). Leukemia is a broad term covering a spectrum of diseases. The first division is between its acute and chronic forms: (i) acute leukemia is characterized by the rapid increase of immature blood cells. This crowding makes the bone marrow unable to produce healthy blood cells. Immediate treatment is required in acute leukemia due to the rapid progression and accumulation of the malignant cells, which then spill over into the bloodstream and spread to other organs of the body. Acute forms of leukemia are the most common forms of leukemia in children; (ii) chronic leukemia is distinguished by the excessive build up of relatively mature, but still abnormal, white blood cells. Typically taking months or years to progress, the cells are produced at a much higher rate than normal cells, resulting in many abnormal white blood cells in the blood. Chronic leukemia mostly occurs in older people, but can theoretically occur in any age group. Additionally, the diseases are subdivided according to which kind of blood cell is affected. This split divides leukemias into lymphoblastic or lymphocytic leukemias and myeloid or myelogenous leukemias: (i) lymphoblastic or lymphocytic leukemias, the cancerous change takes place in a type of marrow cell that normally goes on to form lymphocytes, which are infection-fighting immune system cells; (ii) myeloid or myelogenous leukemias, the cancerous change takes place in a type of marrow cell that normally goes on to form red blood cells, some other types of white cells, and platelets. Within these main categories, there are several subcategories including, but not limited to, Acute lymphoblastic leukemia (ALL), precursor B-cell acute lymphoblastic leukemia (precursor B-ALL; also called precursor B-lymphoblastic leukemia), Acute myelogenous leukemia (AML), Chronic myelogenous leukemia (CML), and Hairy cell leukemia (HCL). Accordingly, disclosed herein, in certain embodiments, is a method for treating Acute lymphoblastic leukemia (ALL), precursor B-cell acute lymphoblastic leukemia (precursor B-ALL; also called precursor B-lymphoblastic leukemia), Acute myelogenous leukemia (AML), Chronic myelogenous leukemia (CML), or Hairy cell leukemia (HCL) in an individual in need thereof, comprising: administering to the individual an amount of a formulation as described herein containing Compound 1. In some embodiments, the leukemia is a relapsed or refractory leukemia. In some embodiments, the leukemia is a relapsed or refractory Acute lymphoblastic leukemia (ALL), relapsed or refractory precursor B-cell acute lymphoblastic leukemia (precursor B-ALL; also called precursor B-lymphoblastic leukemia), relapsed or refractory Acute myelogenous leukemia (AML), relapsed or refractory Chronic myelogenous leukemia (CML), or relapsed or refractory Hairy cell leukemia (HCL).

Symptoms, diagnostic tests, and prognostic tests for each of the above-mentioned conditions are known. See, e.g., Harrison's Principles of Internal Medicine©," 16th ed., 2004, The McGraw-Hill Companies, Inc. Dey et al. (2006), Cytojournal 3(24), and the "Revised European American Lymphoma" (REAL) classification system (see, e.g., the website maintained by the National Cancer Institute).

A number of animal models of are useful for establishing a range of therapeutically effective doses of Compound 1 (or formulations as described herein, containing Compound 1), for treating any of the foregoing diseases.

Compound 1, and Pharmaceutically Acceptable Salts Thereof

"Compound 1" or "1-((R)-3-(4-amino-3-(4-phenoxyphenyl)-1H-pyrazolo[3,4-d]pyrimidin-1-yl)piperidin-1-yl) prop-2-en-1-one" or "1-{(3R)-3-[4-amino-3-(4-phenoxyphenyl)-1H-pyrazolo[3,4-d]pyrimidin-1-yl]piperidin-1-yl}prop-2-en-1-one" or "2-Propen-1-one, 1-[(3R)-3-[4-amino-3-(4-phenoxyphenyl)-1H-pyrazolo[3,4-d]pyrimidin-1-yl]-1-piperidinyl-" or ibrutinib or any other suitable name refers to the compound with the following structure:

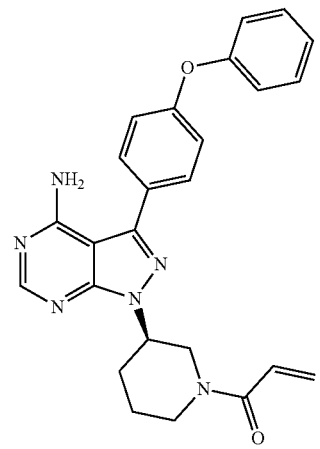 [SMILES: C=CC(=O)N1CCC[C@@H](n2nc(-c3ccc(Oc4ccccc4)cc3)c3c(N)ncnc32)C1]

A wide variety of pharmaceutically acceptable salts is formed from Compound 1 and includes:

acid addition salts formed by reacting Compound 1 with an organic acid, which includes aliphatic mono- and dicarboxylic acids, phenyl-substituted alkanoic acids, hydroxyl alkanoic acids, alkanedioic acids, aromatic acids, aliphatic and aromatic sulfonic acids, amino acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like;

acid addition salts formed by reacting Compound 1 with an inorganic acid, which includes hydrochloric acid, hydrobromic acid, sulfuric acid, nitric acid, phosphoric acid, hydroiodic acid, hydrofluoric acid, phosphorous acid, and the like.

The term "pharmaceutically acceptable salts" in reference to Compound 1, ibrutinib, refers to a salt of Compound 1, which does not cause significant irritation to a mammal to which it is administered and does not substantially abrogate the biological activity and properties of the compound.

It should be understood that a reference to a pharmaceutically acceptable salt includes the solvent addition forms (solvates). Solvates contain either stoichiometric or non-stoichiometric amounts of a solvent, and are formed during the process of product formation or isolation with pharmaceutically acceptable solvents such as water, ethanol, methanol, methyl tert-butyl ether (MTBE), diisopropyl ether (DIPE), ethyl acetate, isopropyl acetate, isopropyl alcohol, methyl isobutyl ketone (MIBK), methyl ethyl ketone (MEK), acetone, nitromethane, tetrahydrofuran (THF), dichloromethane (DCM), dioxane, heptanes, toluene, anisole, acetonitrile, and the like. In one aspect, solvates are formed using, but not limited to, Class 3 solvent(s). Categories of solvents are defined in, for example, the International Conference on Harmonization of Technical Requirements for Registration of Pharmaceuticals for Human Use (ICH), "Impurities: Guidelines for Residual Solvents, Q3C (R3), (November 2005). Hydrates are formed when the solvent is water, or alcoholates are formed when the solvent is alcohol. In some embodiments, solvates of Compound 1 (ibrutinib), or pharmaceutically acceptable salts thereof, are conveniently prepared or formed during the processes described herein. In some embodiments, solvates of Compound 1 (ibrutinib) are anhydrous. In some embodiments, Compound 1 (ibrutinib), or pharmaceutically acceptable salts thereof, exist in unsolvated form. In some embodiments, Compound 1 (ibrutinib), or pharmaceutically acceptable salts thereof, exist in unsolvated form and are anhydrous.

In yet other embodiments, Compound 1 (ibrutinib), or a pharmaceutically acceptable salt thereof, is prepared in various forms, including but not limited to, amorphous phase, crystalline forms, milled forms and nano-particulate forms. In some embodiments, Compound 1 (ibrutinib), or a pharmaceutically acceptable salt thereof, is amorphous. In some embodiments, Compound 1 (ibrutinib), or a pharmaceutically acceptable salt thereof, is amorphous and anhydrous. In some embodiments, Compound 1 (ibrutinib), or a pharmaceutically acceptable salt thereof, is crystalline. In some embodiments, Compound 1 (ibrutinib), or a pharmaceutically acceptable salt thereof, is crystalline and anhydrous.

In some embodiments, Compound 1 (ibrutinib) is prepared as outlined in U.S. Pat. No. 7,514,444.

Certain Terminology

Unless defined otherwise, all technical and scientific terms used herein have the same meaning as is commonly understood by one of skill in the art to which the claimed subject matter belongs. It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include", "includes," and "included," is not limiting.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

The term "about" when used before a numerical value indicates that the value may vary within a reasonable range, such as within +10%, +5% or +1% of the stated value.

As used herein, the term "comprising" is intended to mean that the compositions/formulations and methods, etc., include the recited elements, but do not exclude others. "Consisting essentially of" when used to define compositions/formulations and methods, shall mean excluding other elements of any essential significance to the combination for the intended use, but not excluding elements that do not materially affect the characteristic(s) of the compositions/formulations or methods. "Consisting of" shall mean excluding elements not specifically recited. Embodiments defined by each of these transition terms are within the scope of this invention.

The term "acceptable" or "pharmaceutically acceptable", with respect to a formulation, composition or ingredient, as used herein, means having no persistent detrimental effect on the general health of the subject being treated or does not abrogate the biological activity or properties of the compound, and is relatively nontoxic.

As used herein, "amelioration" of the symptoms of a particular disease, disorder or condition by administration of a particular compound or pharmaceutical composition/formulation refers to any lessening of severity, delay in onset, slowing of progression, or shortening of duration, whether permanent or temporary, lasting or transient that can be attributed to or associated with administration of the compound or composition/formulation.

"Bioavailability" refers to the percentage of Compound 1 dosed that is delivered into the general circulation of the animal or human being studied. The total exposure (AUC$_{(0-\infty)}$) of a drug when administered intravenously is usually defined as 100% bioavailable (F %). "Oral bioavailability" refers to the extent to which Compound 1 is absorbed into the general circulation when the pharmaceutical formulation/composition is taken orally as compared to intravenous injection. In an aspect of the invention, the formulations/compositions described herein are envisioned to have suitable bioavailability.

"Blood plasma concentration" refers to the concentration of Compound 1 in the plasma component of blood of a subject. It is understood that the plasma concentration of Compound 1 may vary significantly between subjects, due to variability with respect to metabolism and/or possible interactions with other therapeutic agents. In accordance with one embodiment disclosed herein, the blood plasma concentration of Compound 1 may vary from subject to subject. Likewise, values such as maximum plasma concentration ($C_{max}$) or time to reach maximum plasma concentration ($T_{max}$), or total area under the plasma concentration time curve (AUC$_{(0-\infty)}$) may vary from subject to subject. Due to this variability, the amount necessary to constitute "a therapeutically effective amount" of Compound 1, or of formulations/compositions described herein containing Compound 1, may vary from subject to subject. Further, formulations/compositions described herein may have a lower $C_{max}$ as compared with the previous e.g., capsule formulations due to the process of absorption after administration. It is challenging to prepare suspensions of ibrutinib that possess both pharmaceutically acceptable properties and desired PK properties, such as a high, comparable or sufficient $C_{max}$.

The term "Bruton's tyrosine kinase," as used herein, refers to Bruton's tyrosine kinase from *Homo sapiens*, as disclosed in, e.g., U.S. Pat. No. 6,326,469 (GenBank Accession No. NP_000052).

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the formulation including a compound as disclosed herein required to provide a clinically significant decrease in disease symptoms without undue adverse side effects. An appropriate "effective amount" in any individual case may be determined using techniques, such as a dose escalation study. The term "therapeutically effective amount" includes, for example, a prophylactically effective amount. An "effective amount" of a compound disclosed herein is an amount effective to achieve a desired pharmacologic effect or therapeutic improvement without undue adverse side effects. It is understood that "an effect amount" or "a therapeutically effective amount" can vary from subject to subject, due to variation in metabolism of Compound 1, age, weight, general condition of the subject, the condition being treated, the severity of the condition being treated, and the judgment of the prescribing physician. By way of example only, therapeutically effective amounts may be determined by routine experimentation, including but not limited to a dose escalation clinical trial.

The terms "inhibits", "inhibiting", or "inhibitor" of a kinase, as used herein, refer to inhibition of enzymatic phosphotransferase activity.

The term "irreversible inhibitor," as used herein, refers to a compound that, upon contact with a target protein (e.g., a kinase) causes the formation of a new covalent bond with or within the protein, whereby one or more of the target protein's biological activities (e.g., phosphotransferase activity) is diminished or abolished notwithstanding the subsequent presence or absence of the irreversible inhibitor.

The term "prophylactically effective amount," as used herein, refers that amount of a formulation applied to a patient which will relieve to some extent one or more of the symptoms of a disease, condition or disorder being treated. In such prophylactic applications, such amounts may depend on the patient's state of health, weight, and the like. It is considered well within the skill of the art for one to determine such prophylactically effective amounts by routine experimentation, including, but not limited to, a dose escalation clinical trial.

The term "individual," "subject" or "patient" as used herein, refers to an animal which is the object of treatment, observation or experiment. By way of example only, a subject may be, but is not limited to, a mammal including, but not limited to, a human.

As used herein, the $IC_{50}$ refers to an amount, concentration or dosage of a particular test compound that achieves a 50% inhibition of a maximal response, such as inhibition of Btk, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

Pharmaceutical Compositions/Formulations

A pharmaceutical formulation (e.g., suspension), as used herein, refers to a mixture of Compound 1 with other chemical components as described herein, such as carriers, diluents, suspending agents, and/or excipients (as applicable). The pharmaceutical formulation facilitates administration of the compound to a mammal. The compounds can be used singly or in combination with one or more therapeutic agents as components of mixtures.

It is an object of the invention to provide formulations with an adequate bioavailability (e.g., a favourable bioavailability compared to the capsule already approved by the FDA). Hence, in an aspect, there is provided a formulation (e.g., a suspension) as described herein, in which:
    the GMR (geometric mean ratio) may range from 75% to 95% (e.g., 80 to 85%) for $C_{max}$;
    the GMR for $AUC_{last}$ may range from 85% to 110% (e.g., from 85 to 100%, or 85 to 95%); and/or
    the GMR for $AUC_{inf}$ (or $AUC_{\infty}$) may range from 80% to 105% (e.g., from 85 to 95%).

Such features relating to exposure may be a part of any of the embodiments disclosed herein.

It should be appreciated that there is considerable overlap between additives used in the formulations described herein (e.g., as between suspending agent and wetting agent).

Thus, the additives (or components of the composition/formulation) mentioned herein should be taken as merely exemplary, and not limiting, of the types of additives that can be included in the compositions or formulations described herein. The amounts of such additives can be readily determined by one skilled in the art, according to the particular properties desired.

Dosing and Treatment Regimens

The dosing and treatment regimens below refer to the amount of Compound 1, and so, in the context of this invention, the amounts can be appropriately extrapolated to apply to the amount of Compound 1 in the formulations (e.g., suspensions) described herein.

In some embodiments, the amount of Compound 1 that is administered to a mammal is from 300 mg/day up to, and including, 1000 mg/day. In some embodiments, the amount of Compound 1 that is administered to a mammal is from 420 mg/day up to, and including, 840 mg/day. In some embodiments, the amount of Compound 1 that is administered to a mammal is about 420 mg/day, about 560 mg/day, or about 840 mg/day. In some embodiments, the amount of Compound 1 that is administered to a mammal is about 420 mg/day. In some embodiments, the amount of Compound 1 that is administered to a mammal is about 560 mg/day. In some embodiments, the $AUC_{0-24}$ of Compound 1 is between about 150 and about 3500 ng*h/ml. In some embodiments, the $AUC_{0-24}$ of Compound 1 is between about 500 and about 1100 ng*h/ml. In some embodiments, Compound 1 is administered orally. In some embodiments, Compound 1 is administered once per day, twice per day, or three times per day. In some embodiments, Compound 1 is administered daily. In some embodiments, Compound 1 is administered once daily. In some embodiments, Compound 1 is administered every other day. In some embodiments, the Compound 1 is a maintenance therapy.

In some embodiments, the amount of Compound 1 that is administered to the pediatric population (e.g., humans up to the age of 18 years) is half that mentioned hereinabove. For example each dose may be between 30 and 140 mg, between 50 and 100 mg or between 60 and 80 mg, for instance about 70 mg (administered in the form of 1 ml suspension as described herein) and the daily dose for the pediatric population is from 150 mg/day up to, and including, 500 mg/day. In some embodiments, the amount of Compound 1 that is administered to the pediatric population is from 210 mg/day up to, and including, 420 mg/day. In some embodiments, the amount of Compound 1 that is administered to the pediatric population is about 210 mg/day, about 280 mg/day, or about 420 mg/day. In some embodiments, the amount of Compound 1 that is administered to a mammal is about 210 mg/day. In some embodiments, the amount of Compound 1 that is administered to a mammal is about 280 mg/day. In some embodiments, the $AUC_{0-24}$ of Compound 1 is between about 150 and about 3500 ng*h/ml. In some embodiments, the $AUC_{0-24}$ of Compound 1 is between about 500 and about 1100 ng*h/ml. In some embodiments, Compound 1 is administered orally. In some embodiments, Compound 1 is administered once per day, twice per day, or three times per day. In some embodiments, Compound 1 is administered daily. In some embodiments, Compound 1 is administered once daily. In some embodiments, Compound 1 is administered every other day. In some embodiments, the Compound 1 is a maintenance therapy.

The formulations containing Compound 1 can be administered for prophylactic, therapeutic, or maintenance treatment. In some embodiments, formulations containing Compound 1 are administered for therapeutic applications (e.g., administered to a subject diagnosed with a hematological malignancy). In some embodiments, formulations containing Compound 1 are administered for therapeutic applications (e.g., administered to a subject susceptible to or otherwise at risk of developing a hematological malignancy). In some embodiments, formulations containing Compound 1 are administered to a patient who is in remission as a maintenance therapy.

In some embodiments, for the pediatric population, the amount of Compound 1 is from 150 mg/day up to, and including, 500 mg/day. In some embodiments, the amount of Compound 1 is from 210 mg/day up to, and including, 420 mg/day. In some embodiments, the amount of Compound 1 is from 200 mg/day up to, and including, 420 mg/day. In some embodiments, the amount of Compound 1 is about 180 mg/day.

In some embodiments, the amount of Compound 1 is about 210 mg/day. In some embodiments, the amount of Compound 1 is about 280 mg/day. In some embodiments, the amount of Compound 1 is about 420 mg/day. In some embodiments, for the pediatric population, the amount of Compound 1 is from 2 mg/kg/day up to, and including, 13 mg/kg/day. In some embodiments, the amount of Compound 1 is from 2.5 mg/kg/day up to, and including, 8 mg/kg/day. In some embodiments, the amount of Compound 1 is from 2.5 mg/kg/day up to, and including, 6 mg/kg/day. In some embodiments, the amount of Compound 1 is from 2.5 mg/kg/day up to, and including, 4 mg/kg/day. In some embodiments, the amount of Compound 1 is about 2.5 mg/kg/day. In some embodiments, the amount of Compound 1 is about 8 mg/kg/day.

As described herein, the formulations of the invention contain a pharmaceutical carrier such as purified water. Hence, doses will be administered as a volume of the suspension. In the case described herein, if a dose is 70 mg of ibrutinib, then the amount of carrier (e.g., purified water) is 1 ml. As indicated herein, the suspension may be more dilute or more concentrated but in any case the volume of the suspension required for a certain dose will be predetermined.

In some embodiments, pharmaceutical formulations described herein include about 70 mg of Compound 1. In some embodiments, a suspension is prepared such that the required dose is available in a predetermined volume (e.g., 1 ml) of a suspension (obtainable via syringe), and thus with each 1 ml including about 70 mg of Compound 1. In some embodiments, 1, 2, 3, 4, or 5 ml doses of a suspension described herein are administered daily. In some embodiments, 2, 3 or 4 ml doses of a suspension described herein are administered daily. In some embodiments, a dose of a suspension described herein is administered once daily. In other embodiments, doses of a suspension described herein are administered multiple times a day.

In some embodiments, a formulation (e.g., suspension) described herein is administered daily. In some embodiments, a formulation (e.g., suspension) described herein is administered every other day.

In some embodiments, a formulation (e.g., suspension) described herein is administered once per day. In some embodiments, a formulation (e.g., suspension) described herein is administered twice per day. In some embodiments, a formulation (e.g., suspension) described herein is administered three times per day. In some embodiments, a formulation (e.g., suspension) described herein is administered four times per day.

In some embodiments, a formulation (e.g., suspension) described herein is administered until disease progression, unacceptable toxicity, or individual choice. In some embodiments, a formulation (e.g., suspension) described herein is administered daily until disease progression, unacceptable toxicity, or individual choice. In some embodiments, a formulation (e.g., suspension) described herein is administered every other day until disease progression, unacceptable toxicity, or individual choice.

The pharmaceutical compositions or formulations described herein may be in any suitable form for single administration of precise dosages (e.g., as a suspension with a measuring syringe, or, as a powder for reconstitution including pre-prepared doses in sachets). Non-limiting examples are powders in vials or ampoules, and aqueous suspension formulations/compositions packaged in single-dose non-reclosable containers. Alternatively, multiple-dose reclosable containers can be used, in which case it is typical to include a preservative in the formulation/composition. In some embodiments, each unit dosage form comprises 70 mg of Compound 1 (and that may be 1 ml, or another suitable predetermined volume, of a suspension described herein). In some embodiments, an individual (e.g., a child) is administered 1 unit dose (70 mg of ibrutinib, e.g., as 1 ml of a suspension described herein) per day. In some embodiments, an individual (e.g., a child) is administered 2 unit doses (140 mg ibrutinib, e.g., as 2×1 ml of a suspension described herein) per day. In some embodiments, an individual (e.g., child) is administered 3 unit doses (210 mg ibrutinib) per day. In some embodiments, an individual is administered 4 unit doses (280 mg ibrutinib) per day.

The foregoing ranges are merely suggestive, as the number of variables in regard to an individual treatment regime is large, and considerable excursions from these recommended values are not uncommon. Such dosages may be altered depending on a number of variables, not limited to the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens can be determined by standard pharmaceutical procedures in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index and it can be expressed as the ratio between $LD_{50}$ and $ED_{50}$. Compounds exhibiting high therapeutic indices are preferred. The data obtained from cell culture assays and animal studies can be used in formulating a range of dosage for use in human. The dosage of such compounds lies preferably within a range of circulating concentrations that include the $ED_{50}$ with minimal toxicity. The dosage may vary within this range depending upon the dosage form employed and the route of administration utilized.

Combination Therapy

Disclosed herein, in certain embodiments, is a method for treating a hematological cancer in an individual in need thereof, comprising: administering to the individual an amount of a formulation (e.g., suspension) as described herein containing Compound 1. In some embodiments, the method further comprises administering a second hematological cancer treatment regimen.

In some embodiments, the second cancer treatment regimen comprises cyclophosphamide, hydroxydaunorubicin, vincristine, and prednisone, and optionally, rituximab.

In some embodiments, the second cancer treatment regimen comprises bendamustine, and rituximab.

In some embodiments, the second cancer treatment regimen comprises fludarabine, cyclophosphamide, and rituximab.

In some embodiments, the second cancer treatment regimen comprises cyclophosphamide, vincristine, and prednisone, and optionally, rituximab.

In some embodiments, the second cancer treatment regimen comprises etoposide, doxorubicin, vinristine, cyclophosphamide, prednisolone, and optionally, rituximab.

In some embodiments, the second cancer treatment regimen comprises dexamethasone and lenalidomide.

Kits/Articles of Manufacture

The kits or packages containing the formulations described herein are designed for use in the methods described herein. The kit can optionally further contain instructions for administering formulation, a container suitable for the formulation, one or more instruments including, without limitation, syringe, pipette, measuring spoon, or the like. Other components for inclusion in the kits would be clear to those skilled in the art, taking into consideration the desired indication and mode of delivery.

For instance, where the formulation is a suspension, it may be packaged in a bottle (e.g., a glass bottle) such as an amber glass bottle with an appropriate adapter and/or closure. Such packaging, in an embodiment also includes measuring instruments for oral dosing of the suspension, which may be a pipette or a syringe. In an embodiment, the measuring instrument is a pipette (e.g., with a tip) and a plunger (e.g., which is not translucent or opaque, but coloured (e.g., following the required regulation, which can be blue and is currently purple), in order to visually aid the measuring of the suspension); in an embodiment the pipette or syringe is made of a suitable polymer such as polypropylene and, further, the plunger should also be made of a certain polymer such as the same polymer as the pipette or, in an embodiment, polyethylene (e.g., high density polyethylene).

A kit typically includes labels listing contents and/or instructions for use, and package inserts with instructions for use. A set of instructions will also typically be included.

In one embodiment, a label is on or associated with the container. In one embodiment, a label is on a container when letters, numbers or other characters forming the label are attached, molded or etched into the container itself; a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein.

EXAMPLES

The following examples are intended to illustrate the present invention and should not be construed as a limitation of the scope of the present invention.

Experimental Section

Example 1

An example of a formulation of the invention may be described as follows:

|  | Quantity (mg/ml) | Role |
|---|---|---|
| Ibrutinib (not salt form) | 70 | API |
| Microcrystalline cellulose and croscarmellose sodium (Avicel RC591) | 12 | Suspending agent |
| Hypromellose (HPMC 2208 3 mPa · s.) | 2.5 | Wetting agent |
| Citric acid•H$_2$O | 0.7328 | Buffer |
| Na$_2$HPO$_4$ | 1.38 | Buffer |
| Sucralose | 1 | Sweetener |
| Benzyl alcohol | 10 | Preservative |
| NaOH all use | q.s. ad pH 6.0 ± 0.1 | pH adjustment |
| cHCl all use | q.s. ad pH 6.0 ± 0.1 | pH adjustment |
| Purified water | q.s. ad 1 ml | solvent |
| Density (g/ml) | 1.020 |  | where Avicel RC591 is used and is a specific mixture of microcrystalline cellulose and croscarmellose sodium (carboxymethylcellulose sodium)

The above formulation details are based on ingredients in 1 ml purified water. Hence starting from 100 ml purified water a corresponding scaled-up version of the above formulation can be prepared (by multiplying the quantity of the ingredients by 100).

Background and Reference Examples

Examples of various suspensions where parabens were employed as the preservative (e.g., sodium methyl paraben and/or sodium ethyl paraben) were tested, and have been successfully developed to support clinical Phase 1 studies (see international patent application WO 2016/164404). The Phase 1 concept was modified (mainly to increase the percentage of parabens) to get a new multi doses concept with a view to supporting Phase III clinical studies. These concepts are depicted in the following table respectively as Composition 1 and Composition 2:

|  | Composition 1 | Composition 2 |
|---|---|---|
| Ibrutinib (non-salt form, free base) | 70 | 70 |
| Microcrystalline cellulose and croscarmellose sodium (Avicel RC591) | 13 | 14 |
| Hypromellose (HPMC 2910 5 mPa · s.) | 2.5 | 2.5 |
| Citric acid•H$_2$O | 1.513 | 1.6160 |
| Na$_2$HPO$_4$ | 1.38 | 1.38 |
| Sucralose | 1 | 1 |
| Na methyl paraben | 1.145 | 1.3740 |
| Na ethyl paraben | 0.575 | 0.6792 |
| NaOH all use | q.s. ad pH 6.0 ± 0.1 | q.s. ad pH 6.0 ± 0.1 |
| cHCl all use | q.s. ad pH 6.0 ± 0.1 | q.s. ad pH 6.0 ± 0.1 |
| Purified water | q.s. ad 1ml | q.s. ad 1 ml |
| Density (g/ml) | 1.021 | 1.022 |

Hence, with respect to the above two suspensions, the total paraben amount was increased by 20% (from Composition 1 to Composition 2), together with other changes such as increase in the suspending agent (microcrystalline cellulose and croscarmellose sodium) concentration and consequently an increase in the amount of citric acid (due to the final target pH).

As consequence of the increased paraben concentration, a crystallization issue has been observed with the suspension Composition 2 after a few months in stability at different storage conditions. Under microscope, nice new needle-shaped crystals were observed in a huge amount. By IR, Raman and MS analysis, the new needle crystals are characterized as potentially being co-crystals of the API and Parabens. As unique consequence of this API-Parabens co-crystallization, the amount of the available paraben preservative resulted to be inferior to that expected, as established by the unexpected failed PET tests (Preservation Efficiency Tests, performed and analyzed according to Pharmacopoeia references e.g., US Pharmacopoeia <51> and Ph.Eur. 5.1.3) reported in the tables below.

Overview of PET Tests and Observation of Crystals:

|  | Methyl paraben (%) | Ethyl paraben (%) | pH | API (mg/ml) | PET result |
|---|---|---|---|---|---|
|  | — | — | 6 | 70 | failed |
|  | 80 | 80 | 5.5 | 70 | failed |
|  | 80 | 80 | 6 | 70 | failed |
|  | 80 | 80 | 6.5 | 70 | failed |
|  | 85 | 85 | 5.5 | 70 | failed |
|  | 85 | 85 | 6 | 70 | failed |
|  | 85 | 85 | 6.5 | 70 | failed |
|  | 90 | 90 | 5.5 | 70 | Pass |
|  | 90 | 90 | 6 | 70 | Pass |
|  | 90 | 90 | 6.5 | 70 | failed |
|  | 95 | 95 | 5.5 | 70 | Pass |
|  | 95 | 95 | 6 | 70 | failed |
|  | 95 | 95 | 6.5 | 70 | Pass |
|  | 100 | 100 | 6 | 70 | Pass |
| Composition 1 but where pH adjusted | 100 | 100 | 5.5 | 70 | Pass |
| Composition 1 | 100 | 100 | 6 | 70 | Pass |
| Composition 1 but where pH adjusted | 100 | 100 | 6.5 | 70 | Pass |
| Composition 2 but where pH adjusted | 120 | 120 | 5.5 | 70 | failed |
| Composition 2 | 120 | 120 | 6 | 70 | failed |
| Composition 2 but where pH adjusted | 120 | 120 | 6.5 | 70 | failed |

For the last three entries (Composition 2 and the same composition but where the pH is adjusted to pH 5.5 and 6.5), (co-)crystals were observed that were needle-shaped.

Hence, it could be seen that the compositions/formulations where the parabens levels were 120% failed the PETs.

The above formulations/compositions could be improved to achieve a more robust preservative system to cover the drug product shelf-life. Further studies were performed (as outlined below) in order to provide alternative/improved suspensions, e.g., those that did not have the drawbacks such as failed PET tests and/or formation of undesired crystalline (e.g., co-crystal) products. For instance, it was desired/sought to achieve suspensions with a more robust preservative system to cover the drug product shelf-life and/or adequate particle size distribution throughout the suspension for instance as described herein.

The above outlines the drive to seek variations of the suspensions and to seek further preservatives for the suspensions.

Study of Solubility of Methyl, Ethyl and Propyl Parabens (Alone or in Presence of Different Amount of Propylene Glycol) at Different Temperatures at pH 6

The thermodynamic solubility of Methyl Ethyl and Propyl parabens (as pure or in mixture with different percentages of Propylene Glycol) was evaluated in buffered solutions. The solubility was evaluated as a function of Hypromellose concentration (0, 2.5 mg/ml, 5 mg/ml and 10 mg/ml) and as a function of temperature (5° C., 20° C. and 40° C.). The saturated paraben solutions were spiked with excess of the active ingredient (ibrutinib), filtered and the ibrutinib/parabens concentration was followed over time (1, 2, 3 and 4 weeks) in the filtered solution.

Results/Conclusion

The addition of propylene glycol may have a slight positive effect on the solubility of the parabens. However, the parabens concentrations in all formulations (and at all temperatures) dropped in function of time after addition of ibrutinib. This was accompanied by several physical observations like the appearance of sticky substances in the vial and additional peaks in the chromatographic data were observed in all 40° C. samples.

Hence, none of these different concepts were suitable for further development. In particular, the methyl/ethyl parabens were not suitable.

Study of New Concepts, Methyl/Ethyl Parabens Vs Other Preservatives 25 samples were prepared in order to test preservative effect, based on the following table, where in each case 70 mg/ml ibrutinib was employed, 1 mg/ml sweetener (sucralose) was employed and pH was adjusted using adjusters mentioned herein:

| | | | (mg/ml) | | |
|---|---|---|---|---|---|
| Concept No. | Suspending agent | Wetting agent | Buffers | Preservative | pH |
| 1 | Avicel RC591 14 mg/ml | HPMC 2910 5 mPas 2.5 mg/ml | Citric acid $H_2O$* (1.4982 mg/ml); $Na_2HPO_4$ (1.38 mg/ml) | Me Pa (1 mg/ml); Et Pa (0.5 mg/ml) | 6 |
| 2 | Avicel RC591 14 mg/ml | HPMC 2910 5 mPas 2.5 mg/ml | 0.2 mg/ml $Na_2HPO_4$ + 1.8 mg/ml $NaH_2PO_4$ 1Q | Me Pa (1 mg/ml); Et Pa (0.5 mg/ml) | 6 |

-continued

| | | | (mg/ml) | | |
|---|---|---|---|---|---|
| Concept No. | Suspending agent | Wetting agent | Buffers | Preservative | pH |
| 3 | Avicel RC591 14 mg/ml | HPMC 2910 5 mPas 10 mg/ml | Citric acid $H_2O^*$ (1.4982 mg/ml); $Na_2HPO_4$ (1.38 mg/ml) | Me Pa (1 mg/ml); Et Pa (0.5 mg/ml) | 6 |
| 4 | Avicel RC591 12 mg/ml | HPC 2910 150-700 mPas 20 mg/ml | Citric acid $H_2O^*$ (1.4982 mg/ml); $Na_2HPO_4$ (1.38 mg/ml) | Me Pa (1 mg/ml); Et Pa (0.5 mg/ml) | 6 |
| 5 | Avicel RC591 12 mg/ml | HPC 2910 150-700 mPas 20 mg/ml | 0.1 mg/ml $Na_2HPO_4$ + 0.9 mg/ml $NaH_2PO_4$ 1Q | $^a$Me Pa (1 mg/ml); $^a$Et Pa (0.5 mg/ml) | 6 |
| 6 | Avicel RC591 14 mg/ml | HPMC 2208 2.5 mg/ml | Citric acid $H_2O^*$ (1.4982 mg/ml); $Na_2HPO_4$ (1.38 mg/ml) | Me Pa (1 mg/ml); Et Pa (0.5 mg/ml salt) | 6 |
| 7 | Avicel RC591 12 mg/ml | HPMC 2208 0.5 mg/ml | 0.1 mg/ml $Na_2HPO_4$ + 0.9 mg/ml $NaH_2PO_4$ 1Q | $^a$Me Pa (1 mg/ml); $^a$Et Pa (0.5 mg/ml) | 6 |
| 8 | Avicel RC591 14 mg/ml | HPMC 2910 5 mPas 2.5 mg/ml | Citric acid $H_2O^*$ (1.4982 mg/ml); $Na_2HPO_4$ (1.38 mg/ml) | Me Pa (1 mg/ml); Et Pa (0.5 mg/ml); Propylene glycol (50 mg/ml) | 6 |
| 9 | Avicel RC591 14 mg/ml | HPMC 2910 5 mPas 2.5 mg/ml | Citric acid $H_2O^*$ (1.4982 mg/ml); $Na_2HPO_4$ (1.38 mg/ml) | Me Pa (1 mg/ml); Et Pa (0.5 mg/ml); propylene glycol (100 mg/ml) | 6 |
| 10 | Avicel RC591 14 mg/ml | HPMC 2910 5 mPas 2.5 mg/ml | Citric acid $H_2O^*$ (1.4982 mg/ml); $Na_2HPO_4$ (1.38 mg/ml) | Me Pa (2 mg/ml); propylene glycol (50 mg/ml) | 6 |
| 11 | Avicel RC591 14 mg/ml | HPMC 2910 5 mPas 2.5 mg/ml | Citric acid $H_2O^*$ (1.4982 mg/ml); $Na_2HPO_4$ (1.38 mg/ml) | Me Pa (1.5 mg/ml); propylene glycol (50 mg/ml) | 6 |
| 12 | Avicel RC591 14 mg/ml | HPMC 2910 5 mPas 2.5 mg/ml | Citric acid $H_2O^*$ (1.4982 mg/ml); $Na_2HPO_4$ (1.38 mg/ml) | Me Pa (1.3 mg/ml); Pr Pa (0.2 mg/ml salt); propylene glycol (50 mg/ml) | 6 |
| 13 | Avicel RC591 14 mg/ml | HPMC 2910 5 mPas 2.5 mg/ml | Citric acid $H_2O^*$ (0.6782 mg/ml); $Na_2HPO_4$ (1.38 mg/ml) | Propylene glycol (200 mg/ml) | 6 |
| 14 | Avicel RC591 14 mg/ml | HPMC 2910 5 mPas 2.5 mg/ml | Citric acid $H_2O^*$ (0.6782 mg/ml); $Na_2HPO_4$ (1.38 mg/ml) | Propylene glycol (160 mg/ml) | 6 |
| 15 | Avicel RC591 14 mg/ml | HPMC 2910 5 mPas 2.5 mg/ml | Citric acid $H_2O^*$ (0.6782 mg/ml); $Na_2HPO_4$ (1.38 mg/ml) | Propylene glycol (120 mg/ml) | 6 |
| 16 | Avicel RC591 14 mg/ml | HPMC 2910 5 mPas 2.5 mg/ml | Citric acid $H_2O^*$ (0.9188 mg/ml); $Na_2HPO_4$ (1.16 mg/ml) | Sorbic acid (1 mg/ml) | 5 |
| 17 | Avicel RC591 14 mg/ml | HPMC 2910 5 mPas 2.5 mg/ml | Citric acid $H_2O^*$ (1.2032 mg/ml); $Na_2HPO_4$ (0.90 mg/ml) | Benzoic acid (2 mg/ml) | 4 |

| Concept No. | Suspending agent | Wetting agent | Buffers | Preservative | pH |
|---|---|---|---|---|---|
| | | | (mg/ml) | | |
| 18 | Avicel RC591 14 mg/ml | HPMC 2910 5 mPas 2.5 mg/ml | Citric acid $H_2O$* (0.6782 mg/ml); $Na_2HPO_4$ (1.38 mg/ml) | Benzyl alcohol (9 mg/ml) | 6 |
| 19 | Avicel RC591 14 mg/ml | HPMC 2910 5 mPas 2.5 mg/ml | Citric acid $H_2O$* (0.6782 mg/ml); $Na_2HPO_4$ (1.38 mg/ml) | Benzyl alcohol (7.5 mg/ml) | 6 |
| 20 | Avicel RC591 14 mg/ml | HPMC 2910 5 mPas 2.5 mg/ml | Citric acid $H_2O$* (0.6782 mg/ml); $Na_2HPO_4$ (1.38 mg/ml) | Benzyl alcohol (6 mg/ml) | 6 |
| 21 | Avicel CL611 20 mg/ml | HPMC 2910 5 mPas 2.5 mg/ml | Citric acid $H_2O$* (1.4982 mg/ml); $Na_2HPO_4$ (1.38 mg/ml) | Me Pa (1 mg/ml); Et Pa (0.5 mg/ml) | 6 |
| 22 | Avicel CL611 20 mg/ml | HPMC 2208 2.5 mg/ml | 0.1 mg/ml $Na_2HPO_4$ + 0.9 mg/ml $NaH_2PO_4$ 1Q | $^a$Me Pa (1 mg/ml); $^a$Et Pa (0.5 mg/ml) | 6 |
| 23 | Avicel CL611 20 mg/ml | HPMC 2208 2.5 mg/ml | 0.2 mg/ml $Na_2HPO_4$ + 1.8 mg/ml $NaH_2PO_4$ 1Q | $^a$Me Pa (1 mg/ml); $^a$Et Pa (0.5 mg/ml) | 6 |
| 24 | Avicel CL611 20 mg/ml | HPMC 2208 2.5 mg/ml | 0.1 mg/ml $Na_2HPO_4$ + 0.9 mg/ml $NaH_2PO_4$ 1Q | $^a$Me Pa (1.2 mg/ml); $^a$Et Pa (0.6 mg/ml) | 6 |
| 25 | Avicel CL611 20 mg/ml | HPC 2910 150-700 mPas 20 mg/ml | 0.1 mg/ml $Na_2HPO_4$ + 0.9 mg/ml $NaH_2PO_4$ 1Q | $^a$Me Pa (1 mg/ml); $^a$Et Pa (0.5 mg/ml) | 6 |

*adjusted during preparation by acid/base addition
$^a$the parabens added as non-ionic form and followed a one pot procedure (all other concepts where parabens are used, i.e. concepts 1-4, 6, 8-12 and 21, the parabens are added as Na salts)

For the avoidance of doubt, in the table above:
Me Pa refers to methylparaben, Et Pa refers to ethylparaben and Pr Pa refers to propyl paraben
1Q refers to $1H_2O$ Thus, completely new preservative systems were tested using propylene glycol, ascorbic acid, benzoic acid or benzyl alcohol and parabens in combination with new excipients or a different process. Avicel RC591 has been compared with CL611; HPMC 2910 5 mPas with HPMC 2208 3 mPas and HPC; the buffer citric acid/$Na_2HPO_4$ with the buffer $Na_2HPO_4$/$NaH_2PO_4$ and the use of parabens as Na salts (in a multi steps process) has been compared with the use of the non-ionic parabens (in one-pot process).

The new 25 concepts were screened in a 1M ASAP (Accelerated Stability Assessment Program) stability study (5, 40 and 60° C. storage conditions), in a 6M lab stability study and in PET tests.

Results for the 25 Samples

The Results of the 1-Month (1M) ASAP (Accelerated Stability Assessment Program) Stability Study (5° C., 40° C. and 60° C. Storage Conditions) Gave the Following General Indications:
API assay, purity profile, pH and suspension appearance resulted in all cases stable and good.
Only in the preservative stability some important differences have been observed between the different concepts. With parabens, a reduction between 1 and 6% has been observed in the assay of samples stored for 1 month (1M) at 60° C. Sorbic acid assay was reduced by about 15%, benzoic acid by about 5% and by only 1% for benzyl alcohol.

The Results of the 6-Month (6M) Lab Stability

The new 25 concepts were principally screened (at different time points) for physical stability: viscosity, yield point, visual aspect and API (co-)crystallization in different stressed conditions.

All suspension viscosities and yield points over time were acceptable. Only the Avicel structure of the sample containing benzoic acid at pH 4, after 6 months (6M) resulted completely broken with no yield point. Avicel is expected to be more stable at 5<pH<9.

Suspension visual aspect (powder settling, water separation, structure breaking, etc.) investigation was done by the observation of samples stored for 6M at rest into a glass cylinder. In conclusion, with all the concepts the suspension in the cylinder resulted in a compact form, not able to flow when the cylinder was left for 10 sec up-side down. No powder settling, no water separation was observed. The only exception was represented by the concept containing Avicel in combination with HPC (Concept 4) which exhibited a water separation of about 2.5 ml in the bottom of the cylinder.

The research of possible new needle-shaped crystals (typical of co-crystals API-parabens), was done by microscope analysis of suspension samples stored/handled in different ways.

All concepts were stored for 1M at 40 and 60° C.: only in concepts 22 and 24 new crystals were found.

All concepts were stored for 6M under cyclic conditions (5° C./12 h-40° C./12 h): after 1M, only seven concepts (from 13 to 20) resulted free of new needle-shaped crystals, while in all the other samples they were observed. Between the acceptable concepts 13 to 20, after 6M storage in cyclic conditions, only in the concept containing benzoic acid as an incipient was new crystallization observed. The other samples were stable.

All concepts were physically stressed by rolling.

All suspension concepts were rolled into a glass vial, closed with a child resistant stopper, at room temperature, horizontally, at a speed of 25 rpm, for 1M. Promising concepts 9, 17, 18, 19 and 20, where no co-crystals were found after 1M rolling and no other issues in other tests were found, were over-stressed by rolling in the same conditions for three months in total and then left for 3 months (3M) at rest at room temperature. Between these concepts, only concepts 18, 19 and 20 were stable. In the concept 9 new crystals were observed while in the concept 17 a possible incipient crystallization was observed.

Sample spiking with co-crystals.

Some concepts were spiked to try to induce a rapid co-crystallization. Concepts containing Methyl and Ethyl paraben, were spiked with few granules of powder of co-crystals of API/Methyl Paraben and API/Et Paraben. After spiking, the samples were homogenized by shaking (by hand), evaluated under microscope (in samples 24 and 25 some crystals were already observed before spiking) and finally stored under cyclic conditions for 6M. In conclusion, after 1M-6M storage under cyclic conditions, all samples showed new needle—shaped crystals.

PET Results and Analysis (for Concepts 17-20)

PET testing was done on all of the concepts, and below the results for the most promising concepts (see above) is shown.

Based on the results obtained from the 25 screened concepts (principally PET results and new needle (co-) crystals formation in one or more of the tested conditions), a first concept selection was done when 2M stability data were available. Only the concepts 17 and 18 (containing respectively benzoic acid and benzyl alcohol as new preservative) were selected for further investigation (see table below).

Concept Selection for Further Development Based on 2M Stability Data

| Concept reference | PET test | New crystals observed in one/more conditions at 2M decision time point |
|---|---|---|
| 1 | Pass | Yes |
| 2 | Pass | Yes |
| 3 | Pass | Yes |
| 4 | Fail | Yes |
| 5 | Pass | Yes |
| 6 | Fail | Yes |
| 7 | Fail | Yes |
| 8 | Pass | Yes |
| 9 | Pass | Yes |
| 10 | Pass | Yes |
| 11 | Fail | Yes |
| 12 | Pass | Yes |
| 13 | Fail | No |
| 14 | Fail | No |
| 15 | Fail | No |
| 16 | Fail | No |
| 17 | Pass | No (No at 2M time point selection, but some new crystals seen at 6M time point) |
| 18 | Pass | No |
| 19 | Fail | No |
| 20 | Fail | No |
| 21 | Pass | Yes |
| 22 | Fail | Yes |

| Organism | Blank at 0 hours | at 14 days | Log reduction 14 days | Result after 14 days | at 28 days | Log reduction 28 days | Result after 28 days |
|---|---|---|---|---|---|---|---|
| | | | Concept 17 | | | | |
| A. brasiliensis | $1.15 \times 10^5$ | <100 | >3.0607 | Pass | <100 | >3.0607 | Pass |
| C. albicans | $3.40 \times 10^5$ | <100 | >3.5315 | Pass | <100 | >3.5315 | Pass |
| P. aeruginosa | $4.95 \times 10^5$ | <100 | >3.6946 | Pass | <100 | >3.6946 | Pass |
| S. aureus | $7.00 \times 10^5$ | <100 | >3.8451 | Pass | <100 | >3.8451 | Pass |
| E. coli | $8.25 \times 10^5$ | <100 | >3.9165 | Pass | <100 | >3.9165 | Pass |
| | | | Concept 18 | | | | |
| A. brasiliensis | $1.15 \times 10^5$ | $6.00 \times 10^2$ | 2.2825 | Pass | <100 | >3.0607 | Pass |
| C. albicans | $3.40 \times 10^5$ | <100 | >3.5315 | Pass | <100 | >3.5315 | Pass |
| P. aeruginosa | $4.95 \times 10^5$ | <100 | >3.6946 | Pass | <100 | >3.6946 | Pass |
| S. aureus | $7.00 \times 10^5$ | <100 | >3.8451 | Pass | <100 | >3.8451 | Pass |
| E. coli | $8.25 \times 10^5$ | <100 | >3.9165 | Pass | <100 | >3.9165 | Pass |
| | | | Concept 19 | | | | |
| A. brasiliensis | $1.15 \times 10^5$ | $1.80 \times 10^3$ | 1.8054 | Pass | $9.50 \times 10^2$ | 2.0830 | Pass |
| C. albicans | $3.40 \times 10^5$ | $3.50 \times 10^3$ | 1.9874 | Failed | <100 | >3.5315 | Pass |
| P. aeruginosa | $4.95 \times 10^5$ | <100 | >3.6946 | Pass | <100 | >3.6946 | Pass |
| S. aureus | $7.00 \times 10^5$ | <100 | >3.8451 | Pass | <100 | >3.8451 | Pass |
| E. coli | $8.25 \times 10^5$ | <100 | >3.9165 | Pass | <100 | >3.9165 | Pass |
| | | | Concept 20 | | | | |
| A. brasiliensis | $1.15 \times 10^5$ | $2.00 \times 10^3$ | 1.7597 | Pass | $2.05 \times 10^3$ | 1.7489 | Pass |
| C. albicans | $3.40 \times 10^5$ | $5.00 \times 10^4$ | 0.8325 | Failed | $5.50 \times 10^2$ | 2.7911 | Pass |
| P. aeruginosa | $4.95 \times 10^5$ | <100 | >3.6946 | Pass | <100 | >3.6946 | Pass |
| S. aureus | $7.00 \times 10^5$ | <100 | >3.8451 | Pass | <100 | >3.8451 | Pass |
| E. coli | $8.25 \times 10^5$ | $3.50 \times 10^2$ | 3.3724 | Pass | <100 | >3.9165 | Pass |

| Concept reference | PET test | New crystals observed in one/more conditions at 2M decision time point |
|---|---|---|
| 23 | Fail | Yes |
| 24 | Fail | Yes |
| 25 | Fail | Yes |

Further Data on Benzyl Alcohol and Benzoic Acid Concepts

A further 13 samples (concepts 26-38), using benzoic acid and benzyl alcohol were prepared in order to test stability and preservative effect, based on the following table, wherein each case 70 mg/ml ibrutinib as free base was employed, 1 mg/ml sweetener (sucralose) was employed and pH was adjusted using adjusters mentioned herein:

| Concept No. | Suspending agent | Wetting agent | Buffers (mg/ml) | Preservative | pH |
|---|---|---|---|---|---|
| 26 | Avicel RC591 12 mg/ml | HPMC 2910 5 mPas 2.5 mg/ml | Citric acid H$_2$O* (0.6782 mg/ml); Na$_2$HPO$_4$ (1.38 mg/ml) | Benzyl alcohol (8 mg/ml) | 6 |
| 27 | Avicel RC591 12 mg/ml | HPMC 2910 5 mPas 2.5 mg/ml | Citric acid H$_2$O* (0.6782 mg/ml); Na$_2$HPO$_4$ (1.38 mg/ml) | Benzyl alcohol (8 mg/ml) | 6.5 |
| 28 | Avicel RC591 12 mg/ml | HPMC 2910 5 mPas 2.5 mg/ml | Citric acid H$_2$O* (0.6782 mg/ml); Na$_2$HPO$_4$ (1.38 mg/ml) | Benzyl alcohol (8 mg/ml) | 5.5 |
| 29 | Avicel RC591 12 mg/ml | HPMC 2910 5 mPas 2.5 mg/ml | Citric acid H$_2$O* (0.6782 mg/ml); Na$_2$HPO$_4$ (1.38 mg/ml) | Benzyl alcohol (10 mg/ml) | 6 |
| 30 | Avicel RC591 14 mg/ml | HPMC 2910 5 mPas 2.5 mg/ml | Citric acid H$_2$O* (0.6782 mg/ml); Na$_2$HPO$_4$ (1.38 mg/ml) | Benzyl alcohol (10 mg/ml) | 6 |
| 31 | Avicel RC591 12 mg/ml | HPMC 2208 3 mPas 2.5 mg/ml | Citric acid H$_2$O* (0.6782 mg/ml); Na$_2$HPO$_4$ (1.38 mg/ml) | Benzyl alcohol (10 mg/ml) | 6 |
| 32 | Avicel RC591 12 mg/ml | HPMC 2910 5 mPas 2.5 mg/ml | Citric acid H$_2$O* (1.2032 mg/ml); Na$_2$HPO$_4$ (0.90 mg/ml) | Benzoic acid (1.28 mg/ml) | 4.5 |
| 33 | Avicel RC591 12 mg/ml | HPMC 2910 5 mPas 2.5 mg/ml | Citric acid H$_2$O* (1.2032 mg/ml); Na$_2$HPO$_4$ (0.90 mg/ml) | Benzoic acid (1.6 mg/ml) | 4.5 |
| 34 | Avicel RC591 12 mg/ml | HPMC 2910 5 mPas 2.5 mg/ml | Citric acid H$_2$O* (1.2032 mg/ml); Na$_2$HPO$_4$ (0.90 mg/ml) | Benzoic acid (1.6 mg/ml) | 4 |
| 35 | Avicel RC591 12 mg/ml | HPMC 2910 5 mPas 2.5 mg/ml | Citric acid H$_2$O* (1.2032 mg/ml); Na$_2$HPO$_4$ (0.90 mg/ml) | Benzoic acid (1.6 mg/ml) | 3.5 |
| 36 | Avicel RC591 12 mg/ml | HPMC 2910 5 mPas 2.5 mg/ml | Citric acid H$_2$O* (1.2032 mg/ml); Na$_2$HPO$_4$ (0.90 mg/ml) | Benzoic acid (2 mg/ml) | 4 |
| 37 | Avicel RC591 14 mg/ml | HPMC 2910 5 mPas 2.5 mg/ml | Citric acid H$_2$O* (1.2032 mg/ml); Na$_2$HPO$_4$ (0.90 mg/ml) | Benzoic acid (2 mg/ml) | 4 |
| 38 | Avicel RC591 12 mg/ml | HPMC 2208 3 mPas 2.5 mg/ml | Citric acid H$_2$O* (1.2032 mg/ml); Na$_2$HPO$_4$ (0.90 mg/ml) | Benzoic acid (2 mg/ml) | 4 |

Concentration of the suspension preservatives benzyl alcohol and benzoic acid was screened at target and limited pH in combination with different Avicel concentrations (12 and 14 mg/ml) and different wetting agent (HPMC 2910 and HPMC 2208), in PET tests and a 2M lab stability study (see above for the methods).

PET Results for Concepts 26-38

Results of the PET test done on the new screened concepts are reported in the table below, where it can be seen that all the concepts passed.

| Organism | Blank at 0 hours | at 14 days | Log reduction 14 days | Result after 14 days | at 28 days | Log reduction 28 days | Result after 28 days |
|---|---|---|---|---|---|---|---|
| \multicolumn{8}{c}{Concept 26} |
| A. brasiliensis | $1.00 \times 10^5$ | $2.50 \times 10^3$ | 1.6021 | Pass | <10 | >4.000 | Pass |
| C. albicans | $2.30 \times 10^5$ | $1.50 \times 10^1$ | 4.1856 | Pass | <10 | >4.3617 | Pass |
| P. aeruginosa | $3.75 \times 10^5$ | <10 | >4.5740 | Pass | <10 | >4.5740 | Pass |
| S. aureus | $3.80 \times 10^5$ | 10 | 4.5798 | Pass | <10 | >4.5798 | Pass |
| E. coli | $5.15 \times 10^5$ | <10 | >4.7118 | Pass | <10 | >4.7118 | Pass |
| \multicolumn{8}{c}{Concept 27} |
| A. brasiliensis | $1.00 \times 10^5$ | $1.50 \times 10^3$ | 1.8239 | Pass | <10 | >4.000 | Pass |
| C. albicans | $2.30 \times 10^5$ | <10 | >4.3617 | Pass | <10 | >4.3617 | Pass |
| P. aeruginosa | $3.75 \times 10^5$ | <10 | >4.5740 | Pass | <10 | >4.5740 | Pass |
| S. aureus | $3.80 \times 10^5$ | <10 | >4.5798 | Pass | <10 | >4.5798 | Pass |
| E. coli | $5.15 \times 10^5$ | <10 | >4.7118 | Pass | <10 | >4.7118 | Pass |
| \multicolumn{8}{c}{Concept 28} |
| A. brasiliensis | $1.00 \times 10^5$ | $1.50 \times 10^3$ | 1.8239 | Pass | <10 | >4.000 | Pass |
| C. albicans | $2.30 \times 10^5$ | <10 | >4.3617 | Pass | <10 | >4.3617 | Pass |
| P. aeruginosa | $3.75 \times 10^5$ | <10 | >4.5740 | Pass | <10 | >4.5740 | Pass |
| S. aureus | $5.80 \times 10^5$ | <10 | >4.7634 | Pass | <10 | >4.5798 | Pass |
| E. coli | $5.15 \times 10^5$ | <10 | >4.7118 | Pass | <10 | >4.7118 | Pass |
| \multicolumn{8}{c}{Concept 29} |
| A. brasiliensis | $1.00 \times 10^5$ | $2.00 \times 10^1$ | 3.6990 | Pass | <10 | >4.000 | Pass |
| C. albicans | $1.50 \times 10^5$ | <10 | >4.1761 | Pass | <10 | >4.1761 | Pass |
| P. aeruginosa | $4.85 \times 10^5$ | <10 | >4.6857 | Pass | <10 | >4.6857 | Pass |
| S. aureus | $5.80 \times 10^5$ | <10 | >4.7634 | Pass | <10 | >4.7634 | Pass |
| E. coli | $3.05 \times 10^5$ | <10 | >4.4843 | Pass | <10 | >4.4843 | Pass |
| \multicolumn{8}{c}{Concept 30} |
| A. brasiliensis | $1.00 \times 10^5$ | $3.00 \times 10^1$ | 3.5229 | Pass | <10 | >4.000 | Pass |
| C. albicans | $1.50 \times 10^5$ | <10 | >4.1761 | Pass | <10 | >4.1761 | Pass |
| P. aeruginosa | $4.85 \times 10^5$ | <10 | >4.6857 | Pass | <10 | >4.6857 | Pass |
| S. aureus | $5.80 \times 10^5$ | <10 | >4.7634 | Pass | <10 | >4.7634 | Pass |
| E. coli | $3.05 \times 10^5$ | <10 | >4.4843 | Pass | <10 | >4.4843 | Pass |
| \multicolumn{8}{c}{Concept 31} |
| A. brasiliensis | $1.00 \times 10^5$ | 10 | 4.000 | Pass | <10 | >4.000 | Pass |
| C. albicans | $1.50 \times 10^5$ | <10 | >4.1761 | Pass | <10 | >4.1761 | Pass |
| P. aeruginosa | $4.85 \times 10^5$ | <10 | >4.6857 | Pass | <10 | >4.6857 | Pass |
| S. aureus | $5.80 \times 10^5$ | <10 | >4.7634 | Pass | <10 | >4.7634 | Pass |
| E. coli | $3.05 \times 10^5$ | <10 | >4.4843 | Pass | <10 | >4.4843 | Pass |
| \multicolumn{8}{c}{Concept 32} |
| A. brasiliensis | $1.05 \times 10^5$ | <10 | >4.0212 | Pass | <10 | >4.0212 | Pass |
| C. albicans | $5.25 \times 10^5$ | <10 | >4.7202 | Pass | <10 | >4.7202 | Pass |
| P. aeruginosa | $4.15 \times 10^5$ | <10 | >4.6180 | Pass | <10 | >4.6180 | Pass |
| S aureus | $3.40 \times 10^5$ | <10 | >4.5315 | Pass | <10 | >4.5315 | Pass |
| E. coli | $4.85 \times 10^5$ | <10 | >4.6857 | Pass | <10 | >4.6857 | Pass |
| \multicolumn{8}{c}{Concept 33} |
| A. brasiliensis | $1.05 \times 10^5$ | <10 | >4.0212 | Pass | <10 | >4.0212 | Pass |
| C. albicans | $5.25 \times 10^5$ | 10 | >4.7202 | Pass | <10 | >4.7202 | Pass |
| P. aeruginosa | $4.15 \times 10^5$ | <10 | >4.6180 | Pass | <10 | >4.6180 | Pass |
| S. aureus | $3.40 \times 10^5$ | <10 | >4.5315 | Pass | <10 | >4.5315 | Pass |
| E. coli | $4.85 \times 10^5$ | <10 | >4.6857 | Pass | <10 | >4.6857 | Pass |
| \multicolumn{8}{c}{Concept 34} |
| A. brasiliensis | $1.05 \times 10^5$ | <10 | >4.0212 | Pass | <10 | >4.0212 | Pass |
| C. albicans | $5.25 \times 10^5$ | <10 | >4.7202 | Pass | <10 | >4.7202 | Pass |
| P. aeruginosa | $4.15 \times 10^5$ | <10 | >4.6180 | Pass | <10 | >4.6180 | Pass |
| S. aureus | $3.40 \times 10^5$ | <10 | >4.5315 | Pass | <10 | >4.5315 | Pass |
| E. coli | $4.85 \times 10^5$ | <10 | >4.6857 | Pass | <10 | >4.6857 | Pass |

| Organism | Blank at 0 hours | at 14 days | Log reduction 14 days | Result after 14 days | at 28 days | Log reduction 28 days | Result after 28 days |
|---|---|---|---|---|---|---|---|
| Concept 35 | | | | | | | |
| A. brasiliensis | $1.05 \times 10^5$ | <10 | >4.0212 | Pass | <10 | >4.0212 | Pass |
| C. albicans | $5.25 \times 10^5$ | <10 | >4.7202 | Pass | <10 | >4.7202 | Pass |
| P. aeruginosa | $4.15 \times 10^5$ | <10 | >4.6180 | Pass | <10 | >4.6180 | Pass |
| S. aureus | $3.40 \times 10^5$ | <10 | >4.5315 | Pass | <10 | >4.5315 | Pass |
| E. coli | $4.85 \times 10^5$ | <10 | >4.6857 | Pass | <10 | >4.6857 | Pass |
| Concept 36 | | | | | | | |
| A. brasiliensis | $1.05 \times 10^5$ | <10 | >4.0212 | Pass | <10 | >4.0212 | Pass |
| C. albicans | $5.25 \times 10^5$ | <10 | >4.7202 | Pass | <10 | >4.7202 | Pass |
| P. aeruginosa | $4.15 \times 10^5$ | <10 | >4.6180 | Pass | <10 | >4.6180 | Pass |
| S. aureus | $3.40 \times 10^5$ | <10 | >4.5315 | Pass | <10 | >4.5315 | Pass |
| E. coli | $4.85 \times 10^5$ | <10 | >4.6857 | Pass | <10 | >4.6857 | Pass |
| Concept 37 | | | | | | | |
| A. brasiliensis | $1.05 \times 10^5$ | <10 | >4.0212 | Pass | <10 | >4.0212 | Pass |
| C. albicans | $5.25 \times 10^5$ | <10 | >4.7202 | Pass | <10 | >4.7202 | Pass |
| P. aeruginosa | $4.15 \times 10^5$ | <10 | >4.6180 | Pass | <10 | >4.6180 | Pass |
| S. aureus | $3.40 \times 10^5$ | <10 | >4.5315 | Pass | <10 | >4.5315 | Pass |
| E. coli | $4.85 \times 10^5$ | <10 | >4.6857 | Pass | <10 | >4.6857 | Pass |
| Concept 38 | | | | | | | |
| A. brasiliensis | $1.05 \times 10^5$ | <10 | >4.0212 | Pass | <10 | >4.0212 | Pass |
| C. albicans | $5.25 \times 10^5$ | <10 | >4.7202 | Pass | <10 | >4.7202 | Pass |
| P. aeruginosa | $4.15 \times 10^5$ | <10 | >4.6180 | Pass | <10 | >4.6180 | Pass |
| S. aureus | $3.40 \times 10^5$ | <10 | >4.5315 | Pass | <10 | >4.5315 | Pass |
| E. coli | $4.85 \times 10^5$ | <10 | >4.6857 | Pass | <10 | >4.6857 | Pass |

Conclusions from Concepts 26-38

Some suspension concepts containing benzoic acid were physically unstable. After two months' observation at low limit pH and after 6M at the target pH, the Avicel structure was completely lost (no yield point measured). This result was probably linked to the very low applied pH, required for the antimicrobial activity of benzoic acid but causing Avicel instability. Avicel is expected to be more stable in the range 5<pH<9.

Some new crystallization was observed in combination with a benzoic acid concept after 6M storage under cyclic conditions and after 3M rolling+3M storage at rest These preliminary results showing possible co-crystallization of ibrutinib with benzoic acid are also confirmed by the disclosures of international patent applications WO 2016/156127 and WO 2016/160604.

The concepts containing benzyl alcohol as preservative, were physically/chemically stable and did not show any (co-)crystallization.

In conclusion, based on these results, benzoic acid was not further evaluated while benzyl alcohol was selected as possible new suspension preservative and further development work.

From the PET results, the target amount of benzyl alcohol was preliminarily selected to be 10 mg/ml: first positive result was obtained with 8 mg/ml and an additional 20% of benzyl alcohol was taken into account for process robustness reasons.

Concepts with Benzyl Alcohol
Wetting Agent

The necessity of a wetting agent like HPMC was tested; the suspension's physical stability and the particle size distribution (PSD) was tested and it was found that the absence of HPMC after 1M storage at 25° C. led to a physically unstable suspension and after 2 months storage at 25° C. led to a shift to a larger particle size (PS). Hence, a formulation/suspension of the invention without HPMC (or another suitable wetting agent) is not recommended. It is supposed that without a wetting agent, particle size may increase (undesirably) due to agglomeration.

A comparison of HPMC 2910 with 2208 was done regarding hydrophobicity, water solubility, free —OH percentage and surface tension with the following results.

HPMC is a thermo-reversible polymer with a specific clouding/gelation temperature linked to the polymer agglomeration by temperature increasing. The clouding/gelation temperature is a function of the polymer concentration, length of the hydrophobic block, and the chemical structure of the polymer. The more hydrophobic the polymer, the lower the clouding/gelation temperature. HPMC 2208 is less hydrophobic than 2910 with a consequent clouding temperature about 20° C. higher than that of HPMC 2910.

HPMC 2208 is less hydrophobic than HPMC 2910 and more water soluble. It is expected consequentially to be more available as a wetting agent for the API (ibrutinib).

Surface tension of a water solution of HPMC 2208 is higher than that of a water solution of HPMC 2910 in the same concentration. HPMC 2208 is expected to be the better wetting agent for the API.

From NMR testing, it was observed that HPMC 2208 3 mPas contains about 18% more free —OH groups than HPMC 2910, aligned with the other results found.

Conclusion

HPMC 2208 3 mPas was therefore selected, in an embodiment, as the new wetting agent for the ibrutinib suspension, as, principally, based on the above, it was expected to be a better wetting agent Other Testing To get the target suspension pH=6.00±0.1, the amount of citric acid.$H_2O$ has been determined to be 0.7302 mg/ml by titration The suspension buffer capacity determination is moderate/good; the suspension density determination is 1.021 g/ml PET robustness study showed positive results A DoE sensitivity study done on the suspension to evaluate the sensitivity of the quality attributes API/Benzyl alcohol/degradant assay and pH versus temperature, oxygen, light and steel showed positive results A DoE robustness study was done on the suspension to evaluate the manufacturing variation (between 90 and 110 w %) of the excipients, with positive results (ongoing)

An edge of failure pH robustness study has been done with the selected concept, at the boundaries of the pH (5.5 and 6.5) with positive results (ongoing)

Process Scale-Up

Example—Pharmaceutical Formulation/Process for Preparing

A pharmaceutical formulation/composition of the invention (a suspension as described above) may be prepared or manufactured by bringing the relevant components into association with each other. An example of the steps includes:

Preparing crystalline Form A of ibrutinib, as described herein (e.g., with reference to the disclosures of WO 2013/184572);

Bringing the remainder of the components into association with one another

Large Scale Preparation

Manufacture process at 50 L scale as below

Add purified water to the compounding vessel 1

Add a solution of HPMC and Benzyl alcohol dissolved in purified water

Add API and stir the preparation mixture until homogenous in vessel 1

Add Avicel to the preparation vessel 1

Add a solution of Sucralose, Na$_2$HPO$_4$ and citric acid H$_2$O in purified water to the vessel 1

Stir the preparation mixture until homogeneous

Measure the preparation pH

Bring the preparation mixture to final volume by addition of purified water

Mix the preparation mixture until homogeneous

Measure final pH

The above processes may also be adapted/amended depending on the components included in the pharmaceutical formulation/composition (e.g., based on particular suspending agents, wetting agents, etc., used).

Biological Examples

Studies are performed to test the safety, tolerability and/or efficacy of the formulations of the invention (particularly the formulations that are suspensions) in subjects (e.g., in the pediatric population) with a disease as defined herein (e.g., chronic lymphocytic leukemia, relapsed/refractory mantle cell lymphoma, etc.). Similar studies may also be performed to test such formulations in combination (as described herein).

What is claimed is:

1. A pharmaceutical formulation in the form of a suspension comprising:
   (i) ibrutinib suspended in a suspending agent, wherein ibrutinib is a compound with the structure of Compound 1,

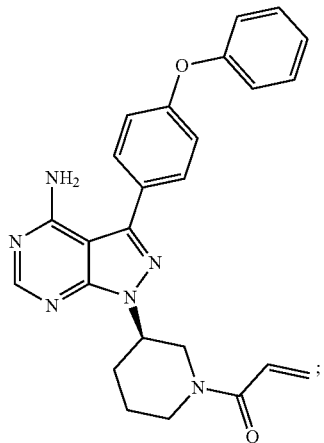

Compound 1 and
   (ii) from 8 mg/ml to 20 mg/ml of benzyl alcohol.

2. The pharmaceutical formulation of claim 1, comprising 10 mg/ml of the benzyl alcohol.

3. The pharmaceutical formulation of claim 1, wherein the suspending agent is an alginate, cellulose ether, methyl cellulose, hydroxyethylcellulose, carboxymethylcellulose, sodium carboxymethylcellulose, microcrystalline cellulose, acacia, tragacanth, xanthan gum, bentonite, carbomer, carrageenan, powdered cellulose or gelatin.

4. The pharmaceutical formulation of claim 1, comprising between 0.1% and 10% w/v of the suspending agent.

5. The pharmaceutical formulation of claim 2, comprising between about 0.5% and 2% w/v of the suspending agent.

6. The pharmaceutical formulation of claim 1, comprising between about 1 mg/ml and 50 mg/ml of the suspending agent.

7. The pharmaceutical formulation of claim 6, comprising between about 5 mg/ml and 20 mg/ml of the suspending agent.

8. The pharmaceutical formulation of claim 1, further comprising one or more wetting agents, one or more buffering agents, one or more pH adjusting agents, one or more additional preservatives, or a sweetener.

9. The pharmaceutical formulation of claim 1, comprising:
   1 ml of a pharmaceutical carrier that is purified water;
   from 20 mg/ml to 200 mg/ml of ibrutinib;
   from 8 mg/ml to 15 mg/ml of benzyl alcohol; and
   from 2 mg/ml to 24 mg/ml of the suspending agent.

10. The pharmaceutical formulation of claim 1, comprising:
    1 ml of a pharmaceutical carrier that is purified water;
    from 60 mg/ml to 80 mg/ml of ibrutinib;
    from 8 mg/ml to 12 mg/ml of benzyl alcohol; and
    from 10 mg/ml to 14 mg/ml of the suspending agent.

11. The pharmaceutical formulation of claim 1, wherein the pharmaceutical formulation does not contain a preservative other than benzyl alcohol.

12. The pharmaceutical formulation of claim 1, further comprising a wetting agent, and wherein the wetting agent is hydroxypropylmethylcellulose (HPMC).

* * * * *